United States Patent
Deschepper et al.

(10) Patent No.: US 9,931,433 B2
(45) Date of Patent: Apr. 3, 2018

(54) TIME-CONTROLLED GLUCOSE RELEASING HYDROGELS AND APPLICATIONS THEREOF

(71) Applicants: Centre National de la Recherche Scientifique (CNRS), Paris (FR); Universite Paris Diderot Paris 7, Paris (FR); Universite Cergy-Pontoise, Cergy (FR); Institut National de la Sante et de la Recherche Medicale (INSERM), Paris (FR)

(72) Inventors: Mickael Deschepper, Maisons-Alfort (FR); Hervé Petite, Paris (FR); Delphine Logeart Avramoglou, Deuil la Barre (FR); Joseph Paquet, Nancy (FR); Emmanuel Pauthe, Cergy (FR); Laurent Bidault, Vaux-sur-Seine (FR); Véronique Larreta Garde, L'Isle Adam (FR)

(73) Assignees: Centre National de la Recherche Scientifique (CNRS), Paris (FR); Universite Paris Diderot Paris 7, Paris (FR); Universite Cergy-Pontoise, Cergy (FR); Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 15/520,603

(22) PCT Filed: Oct. 23, 2015

(86) PCT No.: PCT/EP2015/074648
§ 371 (c)(1),
(2) Date: Apr. 20, 2017

(87) PCT Pub. No.: WO2016/062876
PCT Pub. Date: Apr. 28, 2016

(65) Prior Publication Data
US 2017/0304489 A1   Oct. 26, 2017

(30) Foreign Application Priority Data
Oct. 24, 2014   (EP) .................................. 14306700

(51) Int. Cl.
*A61L 27/38*   (2006.01)
*A61L 27/20*   (2006.01)
(Continued)

(52) U.S. Cl.
CPC ............. *A61L 27/20* (2013.01); *A61L 27/225* (2013.01); *A61L 27/26* (2013.01); *A61L 27/38* (2013.01);
(Continued)

(58) Field of Classification Search
None
See application file for complete search history.

(56) References Cited

FOREIGN PATENT DOCUMENTS

WO   WO 93/17669   9/1993
WO   WO 2008/022183   2/2008
(Continued)

OTHER PUBLICATIONS

Ahmed, *Hydrogel: Preparation, characterization, and applications: A review*, 6 Journal of Advanced Research 105-121 (2015).
(Continued)

*Primary Examiner* — Robert A Wax
*Assistant Examiner* — Melissa S Mercier
(74) *Attorney, Agent, or Firm* — Buchanan Ingersoll & Rooney PC

(57) ABSTRACT

The present invention relates generally to a hydrogel releasing glucose in a time-controlled manner, to medical applications thereof, and to a method for preparing said hydrogel.

20 Claims, 14 Drawing Sheets

(51) Int. Cl.
    A61L 27/22        (2006.01)
    A61L 27/26        (2006.01)
    A61L 27/52        (2006.01)
(52) U.S. Cl.
    CPC ........... *A61L 27/3834* (2013.01); *A61L 27/52* (2013.01); *C12Y 302/01* (2013.01); *A61L 2300/254* (2013.01); *A61L 2400/12* (2013.01)

(56) References Cited

FOREIGN PATENT DOCUMENTS

WO    WO 2011/070529    6/2011
WO    WO-2011070529 A2 *    6/2011    ........... A61K 31/721

OTHER PUBLICATIONS

Anitua et al., *New insights Into and novel applications for platelet-rich fibrin therapies*, 24(5) Trends in Biotechnology 227-234 (May 2006).
Baldwin et al., *Materials for protein delivery in tissue engineering*, 33 Advanced Drug Delivery Reviews 71-86 (1998).
Bensaid et al., *A biodegradable fibrin scaffold for mesenchymal stem cell transplantation*, 24 Biomaterials 2497-2502 (2003).
Cheng et al., *Polymer nanoparticle-mediated delivery of microRNA inhibition and alternative splicing*, 9(5) Mol Pharm 1481-1488 (May 7, 2012).
Dainiak et al., *Gelatin-fibrinogen cryogel dermal matrices for wound repair. Preparation, optimization in vitro study*, 31 Biomaterials 67-76 (2010).
Das, *Preparation Methods and Properties of Hydrogel: A Review*, 5(3) International Journal of Pharmacy and Pharmaceutical Sciences 112-117 (2013).
de Gennes, *Applying recent advances to the study of polymers*, 33(6) Phys. Today 51-54 (Jun. 1980).
Deschepper et al., *Survival and function of mesenchymal stem cells (MSCs) depend on glucose to overcome exposure to long-term severe and continuous hypoxia*, 15(7) J. Cel. Mol. Med. 1505-1514 (2011).
Deschepper et al., *Proangiogenic and Prosurvival Functions of Glucose in Human Mesenchymal Stem Cells Upon Transplantation*, 31 Stem Cells 526-535 (2013).
Fernandez et al., *Biological and engineering design consideration for vascular tissue engineered blood vessels (TEBVs)*, 3 Curr Opin Chem. Eng. 83-90 (Feb. 1, 2014).
Friedenstein et al., *Bone marrow osteogenic stem cells: In vitro cultivation and transplantation in diffusion chambers*, 20 Cell Tissue Kinet 263-272 (1987).
Garg et al., *Scaffold: A Novel Carrier for Cell and Drug Delivery*, 29(1) Critical Reviews in Therapeutic Drug Carrier Systems 1-63 (2012).
Hartgerink et al., *Self-Assembly and Mineralization of Peptide-Amphilphile Nanofibers*, 294 Science 1684-1688 (Nov. 23, 2001).
Jane et al., *Effect of Amylose Molecular Size and Amylopectin Branch Chain Lengthy on Past Properties of Starch*, 69(1) Cereal Chem. 60-65 (1992).
Klak et al., *Gelatin-Alginate Gels and Their Enzymatic Modifications: Controlling the Delivery of Small Molecules*, 13 Macromol. Bioscl. 687-695 (2013).

Klak et al., *Mastered proteolysis of gelatin gel control delivery kinetics of entrapped large molecules*, 8 Soft Matter 4750-4755 (2012).
Konofaos et al., *Nerve Repair by Means of Tubulization: Past, Present, Future*, 29 J. Reconstr. Microsurg. 149-164 (2013).
Lauffer, *Theory of Diffusion in Gels*, 1 Biophysical Journal 205-213 (1961).
Li et al., *Vascular tissue engineering: from in vitro to in situ*, 6 Advanced Review 61-76 (Feb. 2014).
Linnes et al., *A Fibrinogen Based Precision Microporous Scaffold for Tissue Engineering*, 28(35) Biomaterials 5298-5306 (Dec. 2007).
Lundberg, *Cardiovascular Tissue Engineering Research Support at the National Heart., Lung, and Blood Institute*, 112(8) Circ Res 1097-1103 (Apr. 12, 2013).
Neal et al., *Three-Dimensional Elastomeric Scaffolds Designed with Cardiac-Mimetic Structural and Mechanical Features*, 19(5 and 6) Tissue Engineering 793-807 (2013).
Oliveira et al., *Polymer-Based Microparticles in Tissue Engineering and Regenerative Medicine*, 00(00) Biotechnol. Prog. 1-16 (online for 27(4) Biotechnology Progress 987-912) (2011).
Papon et al., *Gelation and Transitions in Biopolymers*, $2^{nd}$ Edition the Physics of Phase Transitions Concepts and Applications 189-213 (2006).
Ronfard et al., *Long-Term Regeneration of Human Epidermis on Third Degree Burns Transplanted with Autologous Cultured Epithelium Grown on a Fibrin Matrix*, 70(11) Transplantation 1588-1598 (Dec. 15, 2000).
Rosso et al., *Smart Materials as Scaffolds for Tissue Engineering*, 203 Journal of Cellular Physiology 465-470 (2005).
Seguchi et al., *Study of Wheat Starch Structures by Sonication Treatment*, 71(6) Cereal Chem. 636-639 (1994).
Singh et al., *Morphological Structural, Thermal, and Rheological Characteristics of Starches Separated from Apples of Different Cultivars*, 53 J. Agric. Food Chem. 10193-10199 (2005).
Sinha et al., *Biodegradable microspheres for protein delivery*, 90 Journal of Controlled Release 261-280 (2003).
Soppimath et al., *Biodegradable polymeric nanoparficles as drug delivery devices*, 70 Journal of Controlled Release 1-20 (2001).
Sperling et al., *The Current Status of Interpenetrating Polymer Networks*, IPNs Around the World Science and Engineering 1-25 (1997).
Steinbach et al., *Polymer Nanoparticles Encapsulating siRNA for Treatment of HSV-2 Genital Infection*, 162(1) J. Control Release 102-110 (Aug. 20, 2012).
Tang et al., *Molecular Design and Applications of Self-Assembling Surfactant-Like Peptides*, 2013 Journal of Nanomaterials 1.9 (2013).
Xia et al., *Tissue Engineering of Cartilage with the Use of Chitosan-Gelatin Complex Scaffolds*, 2 Chitosan Gelatin for Cartilage Engineering 373-380 (2004).
Yang et al., *The Design of Scaffolds for Use in Tissue Engineering. Part II. Rapid Prototyping Techniques*, 8(1) Tissue Engineering 1-11 (2002).
Zhao et al., *Designer Self-Assembling Peptide Materials*, 7 Macromol. Bisoci. 13-22 (2007).
Zimmerman et al., *Cardiac Tissue Engineering for Replacement Therapy*, 8 Heart Failure Reviews 259-269 (2003).

\* cited by examiner

A

B

TIME-CONTROLLED GLUCOSE RELEASING HYDROGELS AND APPLICATIONS THEREOF

CROSS-REFERENCE TO RELATED APPLICATIONS

This application is a U.S. National Stage Application pursuant to 35 U.S.C. § 371 of International Patent Application PCT/EP2015/074648, filed on Oct. 23, 2015, and published as WO 2016/062876 on Apr. 28, 2016, which claims priority to European Patent Application 14306700.7, filed on Oct. 24, 2014, all of which are incorporated herein by reference in their entireties for all purposes.

INTRODUCTION

The present invention relates generally to a hydrogel releasing glucose in a time-controlled manner, to medical applications thereof, and to a method for preparing said hydrogel.

Glucose is the most important carbohydrate in biology known for its role as a source of energy and metabolic intermediate in living cells. The role of glucose in mesenchymal stem cells (MSC) viability and function undergoing continuous severe hypoxia has recently been examined with respect to bone tissue engineering. Multipotent mesenchymal stem cells (MSCs) have indeed shown great potential of inducing the osteogenic phenotype when loaded or directly expended into a porous scaffold which is subsequently implanted into a donor patient. However, the therapeutic effectiveness of those bone constructs was limited by massive death of the transplanted cells after engraftment into the tissue-construct, due notably to oxidative stress, hypoxia, inflammation and lack of pre-existing vascularization within the constructs.

Deschepper et al. (2011; 2013) successfully demonstrated that the survival and function of transplanted MSCs could be greatly enhanced when loaded into glucose-enriched scaffolds, therefore paving the way to overcome the hurdles encountered so far in bone tissue transplant. It was notably showed that the presence of glucose displayed not only pro-survival properties, but also pro-angiogenic properties as it increased peripheral vascularization of implanted tissue constructs. However, those scaffolds did not allow the release of glucose in a controlled manner, at a rate that could match MCS demand for this carbohydrate over an extended period of time.

The present invention thus proposes to address the above-mentioned limitation, by providing a mixed hydrogel in which the rate of glucose released can be tailored and prolonged over several weeks. The hydrogel proposed herein further displays a homogeneous structure, a lack of syneresis and good mechanical properties.

In particular, the hydrogel of the invention contains in its liquid phase a polymer of glucose, as well as an enzyme capable of gradually hydrolysing said polymer into glucose. This polymer plays several roles: it acts not only as a source of glucose which does not alter cellular osmotic properties, but also as a viscosigen agent which limits the diffusion rate of both glucose and the hydrolysing enzyme. This hydrogel is further capable of containing biomaterial such as cells or tissue or any derivative thereof, as well as polymeric particles as reservoir of the hydrolysing enzyme.

The present invention thus provides for the first time a time-controlled glucose releasing hydrogel, medical devices comprising said hydrogel, as well as biomedical applications thereof. A method for preparing said hydrogel and a kit for preparing such hydrogel are also provided.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, nomenclatures used herein, and techniques for preparing hydrogels are those well-known and commonly used in the art.

Such techniques are fully explained in the literature, such as by Ahmed (2013) and Das (2013).

The hydrogel proposed by the present invention can be used to achieve a controlled delivery of glucose.

So, in a first aspect, the present invention is directed to a time-controlled glucose releasing hydrogel, comprising:
a) a water-containing gelified polymer;
b) a glucose polymer entrapped in polymer a); and
c) at least one enzyme capable of hydrolysing the glucose polymer b) into glucose, said enzyme being entrapped in polymer a).

Besides an homogenous structure, good mechanical properties and a substantial lack of syneresis (leaking of liquid phase), the hydrogel of the invention is particularly advantageous as it allows a prolonged release of glucose which can last for up to several weeks, thanks to the gradual degradation of a glucose polymer by a specific hydrolysing enzyme. The presence of this enzyme combined with a glucose polymer is thus critical to achieve this time-controlled release. Indeed, as demonstrated in the Examples hereafter, if the enzyme is omitted from the hydrogel and the glucose polymer is replaced by glucose monomers, the release of glucose occurs on a much shorter timeline, with an almost immediate release of an important quantity of glucose rapidly followed by a release of a small quantity of glucose, which is not desirable.

Thus, the above mentioned components a) b) and c) of the hydrogel represent the minimal elements to achieve a satisfying release of glucose over a prolonged period, without any major peak in glucose concentration.

This hydrogel may further be prepared from biodegradable polymers as further described below, which makes it suitable for biomedical applications.

In addition, one skilled in the art would readily understand that, in the context of the present invention, said water-containing gelified polymer should not be hydrolysable by enzyme c), in particular it should not be hydrolysable, or at least not substantially hydrolysable, by said enzyme into glucose.

Thus, according to a preferred embodiment of the present invention, the time-controlled glucose releasing hydrogel is as defined above, with the proviso that said water-containing gelified polymer a) is not hydrolysable by enzyme c).

The term "hydrogel" refers herein to an insoluble three-dimensional (3-D) network of hydrophilic homopolymers, co-polymers and/or macromers with a high capacity of swelling in aqueous environments. Gels have the property of being elastic solids and very rich in solvent. In particular, for hydrogels, the solvent is water. As indicated above, the hydrogel according to the invention comprises at least three main components. The term "comprising" or "containing" means herein that the listed elements are required or mandatory but that (an)other optional element(s) may or may not be present.

By "time-controlled", "extended", "prolonged" release or delivery, it is meant herein a linear or almost-linear release or delivery of a molecule of interest. As explained above, this effect is accomplished herein by gradual degradation by the hydrolysing enzyme c) of the glucose polymer b) into glucose. A linear release means that the amount of the molecule of interest (i.e. glucose) released over time remains relatively constant during the desired time frame. In the context of the present invention, the release of glucose within the hydrogel can be maintained more or less constant for at least two weeks. Said release is generally preceded by an initial burst in glucose delivery. As well known to the skilled person in the art, the diffusion of a molecule in space may be assessed according to Fick's second law, as follows:

$$\frac{\partial \phi}{\partial t} = D \frac{\partial^2 \phi}{\partial x^2}$$

where:
- $\phi$ is the concentration in dimensions of [(amount of molecule) length$^{-3}$];
- t is time [s];
- D is the diffusion coefficient in dimensions of [length$^2$ time$^{-1}$]; and
- x is the position [length].

Further details for predicting and/or measuring the diffusion of a molecule of interest from an hydrogel are provided in the Examples of the present application, as well as by Lauffer M A (1961), and by Klak et al. (2012, 2013).

By "gelified polymer", it is meant a polymer forming a gel, e.g. by sol/gel phase transition, Accordingly, by "water-containing gelified polymer", it is meant herein a gelified polymer, natural, synthetic, or semi-synthetic in which water is the dispersion medium. One skilled in the art would understand that such polymers can be prepared by using water-soluble gellable monomers or polymers. The term polymer includes copolymers, that can be obtained by copolymerization of at least two different types of constituent units, such as units of two different monomers, or units of two different polymers. Polymers of natural origin, such as proteins or polysaccharides, are non-toxic and biocompatible, while the mechanical and kinetic properties of hydrogels made of synthetic polymers may be more easily defined and tunable.

In the context of the present invention, biodegradable water-containing gelified polymers are particularly preferred as they can dissolve within a period that is suitable for in vivo applications, notably if the hydrogel of the invention is implanted in a subject. For example, an appropriate biodegradable polymer according to the invention may dissolve in less than one year, and more preferably in less than six months. This period may nevertheless vary depending on the site of implantation, and/or the size of the loss/nature of the biological material that needs to be treated in the subject.

Particularly preferred polysaccharide water-containing gelified polymers according to the invention are biodegradable and include, without limitation, alginates, pectins, chitosan, carrageenans, chitin, cellulose, callose, laminarin, chrysdaminarin, xylan, arabinoxylan, mannan, fucoidan, arabinoxylans, dextran, galactomannan, and derivatives thereof, that have been dissolved into water and gelified. Alginates, pectins, chitosan, carrageenans, chitin, cellulose, callose, laminarin, chrysolaminarin, xylan, arabinoxylan, mannan, fucoidan, arabinoxylans, dextran, galactomannan, and derivatives thereof are indeed polysaccharide water-soluble gellable polymers. Besides, as explained above, said polysaccharide water-containing gelified polymers are not hydrolysable by said enzyme c). It is within the skill of the person in the art to select the appropriate combination of polysaccharide water-containing gelified polymers and enzyme c), such that said polymer is not hydrolyzed within the hydrogel by said enzyme. For illustrative purposes, should the skilled person in the art wish to use cellulose as a polysaccharide water-containing gelified polymer a), one should avoid selecting cellobiosidases as enzyme c).

Particularly preferred protein water-containing gelified polymers according to the invention are biodegradable and include, without limitation, silk proteins such as silk fibroin, soy proteins, milk proteins such as casein, wheat proteins such as globulins, gliadins or glutenins, linen proteins, egg proteins, albumin, elastin, myosin, actin, myoglobin, polylysine, polyglutamine, self-assembling peptides such as those described by Hartgerink et al. (2001), by Zhao et al. (2007) and by Tang et al. (2013), proteins comprising RGD sequence(s) such as fibronectin, vitronectin, gelatin, osteopontin, collagens, thrombospondins, fibrinogen, von Willebrand factor, and derivatives thereof, that have been dissolved into water and gelified. Silk proteins, soy proteins, milk proteins, wheat proteins, linen proteins, egg proteins, albumin, elastin, myosin, actin, myoglobin, polylysine, polyglutamine, self-assembling peptides, proteins comprising RGD sequence(s), and derivatives thereof are indeed protein water-soluble gellable polymers.

More particularly preferred protein water-containing gelified polymers according to the invention are fibrin and gelatin, more preferably fibrin.

Fibrin is a protein network resulting from polymerization of fibrinogen hydrolysed by thrombin, which is naturally produced by the body after injury, but can also be recombinantly engineered. Fibrin plays a key role in wound healing and hemostasis where it forms a dynamic three-dimensional network that obstructs the vascular gap. Its interest also relies on its ability to serve as a provisional matrix for various cells such as Human Mesenchymal Stromal Cells or fibroblasts. Fibrin gels have shown promising structural and biological properties for clinical applications in tissue engineering and damaged tissue regeneration; they can be used in the form of fibrin glue and have been optimized for tissue sealing (Rosso et al., 2005; Ben-saïd et al., 2002; Sperling et al., 1997; Ronfard et al., 2000; Anitua et al., 2006; Linnes et al., 2007). Should the hydrogel of the invention be used in biomedical applications, e.g. implanted in a subject, said fibrin can preferably be prepared from fibrinogen isolated from a blood sample of said subject, in order to reduce the risks of disease transmission as well as immunogenic reactions.

Besides, should the protein water-containing gelified polymer a) of the invention be fibrin, the hydrogel of the invention may further comprise aprotinin, in order to prevent any proteolytic degradation of said polymer.

Gelatin, on the other hand, is an irreversible hydrolysed form of collagen, formed by breaking apart its natural triple-helix structure into single-strand molecules. Its interest lies in its lack of immunogenicity by comparison to collagen, its ability to retain informational signaling capacity such as the RGD sequence, and, last importantly, its complete reabsorbability in vivo (Xia et al. 2004; Dainiak et al. 2010).

Many pharmaceutically acceptable synthetic water-containing gelified polymers may be used by one skilled in the art. By "pharmaceutically acceptable", it is meant herein that those polymers are compatible with the other components of the hydrogel, and are not deleterious to the recipient thereof. For illustrative purposes, such polymers may be selected, though not limited to, the group consisting of polyethylene oxide (PEO), polyacrylic acid (PAA), poly(propylene oxide) (PPO), polyethyl hydroxide (PEH), polyvinyl alcohol (PVA), N-isopropylacrylamide (NIPAM), polyacrylamide (PAM), polyvinyl sulfone (PVS), and derivatives thereof, that have been dissolved into water and gelified. Polymers could also be synthesized from methylmethacrylate, N-vinylpyrrolidone (NVP), polyethylene glycol (PEG), and derivatives thereof, that have been dissolved into water and gelified.

Alternatively, one skilled in the art may wish to use a copolymer of the above mentioned water-containing gelified polymers, such as a copolymer of (a) protein(s) and/or of (a) polysaccharide(s) and/or of (a) synthetic water-containing gelified polymer(s). Said copolymer may notably be a semi-synthetic polymer. Semi-synthetic polymers can be of particular interest as they exhibit the advantageous properties of both natural and synthetic polymers. Examples of copolymers according to the invention include, without limitation, methacrylated, acrylated, or vinylated peptides or proteins as defined above, such as a composite of fibrin and acrylate, or a composite of collagen and acrylate, or the triblock polymer PEO-PPO-PEO or PPO-PEO-PPO (Garg et al., 2012).

According to a preferred embodiment, the time-controlled glucose releasing hydrogel of the invention is as defined above, with the proviso that said water-containing gelified polymer is not a polysaccharide. More preferably, said water-containing gelified polymer is a protein polymer, a synthetic polymer, or a combination thereof.

For a complete review of water-soluble gellable polymers that are suitable to generate hydrogels, and of synthesis methods thereof, one skilled in the art may further refer to Ahmed (2013).

The diffusion of the enzyme in the gel can be limited thanks to the viscosigen properties of the selected glucose polymer; the higher this viscosity is, the slower said diffusion is.

According to a preferred embodiment, the glucose polymer b) has a molecular weight of at least 100 kDa, more preferably of at least 200 kDa, and most preferably of at least 300 kDa. This preferred molecular weight allows the maintenance of the structure of the hydrogel during its formation, and contributes to avoid a rapid release of glucose polymer from the hydrogel.

For the purposes of the invention, particularly preferred glucose polymers can be selected by the skilled practitioner from the group consisting of starch, amylose, amylopectin, glycogen, maltodextrins, cyclodextrins polymers, isomaltose polymers, icodextrins, malto-oligosaccharides, dextran, cellulose, pullulan, and derivatives thereof. More preferably, glucose polymers according to the invention are selected from the group consisting of starch, amylose, amylopectin, glycogen, maltodextrins, cyclodextrins polymers, isomaltose polymers, icodextrins, malto-oligosaccharides, dextran, cellulose, and derivatives thereof. Examples of malto-oligosaccharides according to the invention include, without limitation, maltoheptose, maltohexose, maltopentose, maltotetrose, or maltotriose.

Most preferably, the glucose polymer of the hydrogel according to the invention is starch. Indeed, as demonstrated by the Inventors, the starch is not only an excellent source of glucose polymer, but exhibits as well viscosigen properties which limit its leak from the gel and contribute to an extended release of glucose in the hydrogel system of the invention. Starch may also exhibit different viscosity profiles depending upon its botanical origin (Jane et al., 1992; Seguchi et al. 1994; Singh et al., 2005): the Inventors have indeed observed that better hydrogel homogeneity and a more prolonged release of glucose could be reached with wheat starch than with corn starch, rice starch and potato starch, in descending order. Accordingly, the glucose polymer b) of the hydrogel is most preferably wheat starch. The Inventors further discovered that the use of starch of any origin does not affect the gelification of polymer a), in particular fibrin, to obtain the hydrogel of the invention, which thus remains homogenous and substantially free of syneresis.

As indicated above, the glucose polymer b) is "entrapped" or "enmeshed" in the water-containing gelified polymer a) in order to form a continuous network of polymer chains, that is to say said glucose polymer b) is embedded partially or wholly in the water-containing gelified polymer a). The glucose polymer b) concentration in the hydrogel of the invention is preferably ranging from about 0.5% (w/v) to about 15% (w/v), more preferably from about 0.75% (w/v) to about 10% (w/v), more preferably from about 0.85% (w/v) to about 8% (w/v), and even more preferably from about 1% (w/v) to about 4% (w/v), and most preferably is from 1% to 2% (w/v). One skilled in the art would nevertheless understand that this concentration may vary in the above indicated ranges depending upon the nature of the glucose polymer (e.g. starch, amylose, amylopectin, etc.).

According to a preferred embodiment, the hydrogel according to the invention further comprises glucose (i.e. in the form of monomers) in addition to glucose polymer b). Indeed, the presence of glucose in the form of monomers in the hydrogel can lead to an almost immediate burst release of said glucose from the hydrogel, which will be followed by a prolonged release of other monomers of glucose through the gradual degradation by the hydrolysing enzyme c) of the glucose polymer b). This preferred embodiment, though not absolutely required, can be particularly advantageous for example to maximize the survival and proper functionality of a biological material entrapped in the hydrogel, which is intended to be administered to a subject in need thereof.

Said monomers of glucose are also preferably "entrapped" or "enmeshed" in the water-containing gelified polymer a).

It shall be further understood that it is within the skill of the person in the art to select the enzyme or combination of enzymes that is capable of hydrolysing the glucose polymer b) of the hydrogel into glucose, or in other words to select the enzyme or combination of enzymes that specifically hydrolyses said glucose polymer b). Accordingly, said enzyme capable of hydrolysing the glucose polymer b) may preferably be selected from the group consisting of α-glucosidases, β-glucosidases, dextrinases, maltodextrinases, α-amylases, β-amylases, maltohydrolases, cellobiosidases, and combinations thereof, depending upon the substrate of the selected enzyme.

For example, one skilled in the art may use any commercially available enzyme, such as a glucan 1,4 α-glucosidase (EC: 3.2.1.3) or a α-glucosidase (EC: 3.2.1.20) to hydrolyse starch, amylose, glycogen, isomaltose, amylopectin, or cyclodextrin into glucose; a sucrose α-glucosidase (EC: 3.2.1.48) to hydrolyse isomaltose or maltose into glucose; a cyclomaltodextrinase (EC: 3.2.1.54) to hydrolyse cyclodextrin into glucose; a glucan 1,6 α-glucosidase (EC: 3.2.1.70) to hydrolyse dextran into glucose; a combination of cellulase (EC: 3.2.1.4) and glucan 1,4 β-glucosidase (EC: 3.2.1.74) to successively hydrolyse cellulose into cellobiose, cellopentose and/or cellotriose, and said cellobiose, cellopentose and/or cellotriose into glucose; a combination of α-amylase (EC: 3.2.1.1) and glucan 1,4 α-glucosidase (EC: 3.2.1.3) to successively hydrolyse starch, glycogen or malto-oligosaccharides into maltose, and said maltose into glucose; a combination of α-amylase (EC: 3.2.1.1) and sucrose α-glucosidase (EC: 3.2.1.48) to successively hydrolyse starch, glycogen or malto-oligosaccharides into maltose, and said maltose into glucose; a combination of β-amylase (EC: 3.2.1.2) and glucan 1,4 α-glucosidase (EC: 3.2.1.3) to successively hydrolyse starch, amylopectin, amylose, maltodextrin into maltose, and said maltose into glucose; a combination of β-amylase (EC: 3.2.1.2) and sucrose α-glucosidase (EC: 3.2.1.48) to successively hydrolyse starch, amylopectin, amylose, maltodextrin into maltose, and said maltose into glucose; a combination of cyclomaltodextrinase (EC: 3.2.1.54) and glucan 1,4 α-glucosidase (EC: 3.2.1.3) to successively hydrolyse amylopectin into maltose, and said maltose into glucose; a combination of cyclomaltodextrinase (EC: 3.2.1.54) and sucrose α-glucosidase (EC: 3.2.1.48) to successively hydrolyse amylopectin into maltose, and said maltose into glucose; a combination of glucan 1,4 α-maltohydrolase (EC: 3.2.1.133) and glucan 1,4 α-glucosidase (EC: 3.2.1.3) to successively hydrolyse starch into maltose, and said maltose into glucose; a combination of glucan 1,4 α-maltohydrolase (EC: 3.2.1.133) and sucrose α-glucosidase (EC: 3.2.1.48) to successively hydrolyse starch into maltose, and said maltose into glucose; a combination of cellulose 1,4 β-cellobiosidase (EC: 3.2.1.176) and glucan 1,4 β-glucosidase (EC: 3.2.1.74) to successively hydrolyse cellulose into cellobiose, and said cellobiose into glucose; a combination of pullulanase (EC: 3.2.1.41) and sucrose α-glucosidase (EC: 3.2.1.48) to successively hydrolyse glycogen into maltose, and said maltose into glucose; a combination of pullulanase (EC: 3.2.1.41) and glucan 1,4 α-glucosidase (EC: 3.2.1.3) to successively hydrolyse glycogen into maltose, and said maltose into glucose; a combination of isoamylase (EC: 3.2.1.68) and sucrose α-glucosidase (EC: 3.2.1.48) to successively hydrolyse glycogen into maltose, and said maltose into glucose; a combination of pullulanase (EC: 3.2.1.41) and glucan 1,4 α-glucosidase (EC: 3.2.1.3) to successively hydrolyse pullulan into glucose, maltose and maltotriose, and said maltose and maltotriose into glucose; a combination of isoamylase (EC: 3.2.1.68) and glucan 1,4 α-glucosidase (EC: 3.2.1.3) to successively hydrolyse glycogen into maltose, and said maltose into glucose.

Accordingly, should the glucose polymer b) of the invention be starch, the enzyme c) of the hydrogel is preferably a α-glucosidase as described above, or a combination thereof with a α- or β-amylase or a α-maltohydrolase.

The concentration of enzyme c) in the hydrogel is preferably set to obtain an enzymatic activity preferably ranging from about $1.10^{-6}$ µmol·min$^{-1}$·mg$^{-1}$ to about $1.10^{-2}$ µmol·min$^{-1}$·mg$^{-1}$, more preferably from about $1.10^{-5}$ µmol·min$^{-1}$·mg$^{-1}$ to about $1.10^{-3}$ µmol·min$^{-1}$·mg$^{-1}$, even more preferably from about $2.10^{-5}$ µmol·min$^{-1}$·mg$^{-1}$ to about $7.10^{-4}$ µmol·min$^{-1}$·mg$^{-1}$, and yet even more preferably from about $5.10^{-5}$ µmol·min$^{-1}$·mg$^{-1}$ and to about $5.10^{4}$ µmol·min$^{-1}$·mg$^{-1}$. One skilled in the art would nevertheless understand that the concentration in enzyme may vary in the above indicated ranges depending upon the nature of the glucose polymer to be hydrolyzed (e.g. starch, amylose, amylopectin, etc.) and the nature of the selected hydrolyzing enzyme(s).

It is also well known to the skilled person in the art that the above listed enzymes display an optimal hydrolysing capacity (i.e. their specific enzymatic activity) at body temperature (i.e. about 37° C. in humans) and physiological pH (i.e. pH 7.4), which is highly advantageous for in vivo applications, notably if the hydrogel of the invention needs to be implanted in a subject. Thereby, the glucose polymer b) can be easily processed by the enzyme upon implantation in said subject. Those enzymes may nevertheless be active between 25° C. and 42° C. and/or at a pH comprised between pH 7 and pH 7.5, albeit with a different efficacy.

Furthermore, as indicated above, said enzyme c) is "entrapped" or "enmeshed" in the water-containing gelified polymer a) in order to allow the gradual hydrolysis of the glucose polymer b) into glucose, that is to say said enzyme is embedded partially or wholly in the water-containing gelified polymer a).

In a further advantageous embodiment of the invention, the enzyme c) of the hydrogel is more particularly entrapped within polymeric particles d) in polymer a). That is to say that said enzyme c) is encapsulated in (i.e. surrounded by, or absorbed) polymeric particles d) which are themselves embedded partially or wholly in the water-containing gelified polymer a). Should a combination of at least two enzymes be used in the hydrogel to achieve the hydrolysis of glucose polymer b), said enzymes can thus be either all entrapped within polymeric particles d) in polymer a); or one enzyme can be entrapped within polymeric particles d) in polymer a) and the other one can be free within polymer a) (i.e. not entrapped within polymeric particles d)). The former embodiment is nevertheless preferred herein.

The Inventors have indeed observed a considerably prolonged release of glucose from the glucose polymer b), by up to 50 to 70%, when the enzyme c) of the hydrogel is encapsulated in polymeric particles, more particularly in nanoparticles. This prolonged release is possible as encapsulation in such particles not only slow down the diffusion rate of the enzyme within the hydrogel, thereby modifying the quantity of enzyme capable of acting locally, but also protect said enzyme from proteolysis. Besides, depending upon the nature of the polymeric particles (degradable or not), the diffusion of the enzyme can be further facilitated by the natural degradation and dissolution of said particles. Notably, the degradation profile of these particles that affects diffusion, and determines their half-life, depends on parameters such as size of the particles, polymer molecular weight, copolymer ratios, hydrophilicity, etc. It is within the skill of the person in the art to adjust these parameters in order to control the release of enzyme (Sinha et al., 2003), and hence of glucose.

In the context of the present invention, it is more particularly preferred to adjust these parameters so that the half-life of said particles is of at least two weeks, preferably three weeks, more preferably four weeks, five weeks and most preferably six weeks. In order to reach such half-life, a predominantly critical parameter is the size of the polymeric particles.

Polymeric particles that are 1 to 700 µm in diameter are generally considered to be microparticles, whereas particles 1 to 1000 nm in diameter are said to be nanoparticles. According to a preferred embodiment of the invention, the polymeric particles d) are nanoparticles. The term "nanoparticles" includes "nanospheres", which are solid spherical nanoparticles, as well as "nanocapsules", which are liquid or semi-liquid nanoparticles. Nanoparticles are widely used in biomedical applications, including controlled drug delivery, tissue engineering scaffold, bio-adhesive, and cell culture matrix. For a detailed review of polymeric particles, in particular micro- and nanoparticles, one skilled in the art may refer to Baldmin et al. (1998), Oliveira et al. (2011), Steinbach et al. (2012) and Cheng et al. (2012).

As mentioned above, it is within the skill of the person in the art to adjust the size of the polymeric particles in order to achieve the desired delivery of the enzyme c) that subsequently hydrolyses the glucose polymer b) into glucose. A smaller particle size, such as the one of nanoparticles, is generally desirable, as it not only alters the rate of enzyme release due to different surface-to-volume ratios but also facilitates intracellular uptake of glucose which is particularly useful for in vivo or in vitro applications. Accordingly, the size of the polymeric particles used in the hydrogel of the invention is preferably comprised between 10 nm and 1 µm, preferably between 100 nm and 400 nm.

Polymeric particles can be produced from a number of non-biodegradable and biodegradable polymers, of both synthetic and natural origin. For illustrative purposes, biodegradable polymers suitable for the purposes of the invention may be selected, though not limited to, the group consisting of alginate, chitin, gelatin, collagen, albumin, poly(lactic) acid (PLA), poly(glycolic) acid (PGA), poly (lactic-co-glycolic) acid (PLGA), polyhydroxybutyrate (PHB) poly(hydroxybutyrate-co-valerate) (PHBV), polycaprolactone (PCL), and derivatives thereof, while non-biodegradable polymers may be selected, though not limited to, the group consisting of poly(methyl methacrylate) (PMMA), poly(cyanoacrylate) (PCA), and derivatives thereof. One skilled in the art would readily understand that the polymers used to form polymeric particles should preferably differ from polymer a). In other words, if polymer a) is:

albumin, the polymeric particles are not albumin particles; or
gelatin, the polymeric particles are not gelatin particles.

More preferably, said biodegradable polymers are selected from the group consisting of poly(lactic) acid (PLA), poly(glycolic) acid (PGA), poly(lactic-co-glycolic) acid (PLGA), polyhydroxybutyrate (PHB) poly(hydroxybutyrate-co-valerate) (PHBV), polycaprolactone (PCL), and derivatives thereof, while non-biodegradable polymers are selected from the group consisting of poly(methyl methacrylate) (PMMA), poly(cyanoacrylate) (PCA), and derivatives thereof.

In the context of the present invention, biodegradable polymeric particles are particularly preferred as they can dissolve within a period that is suitable for in vivo applications, notably if the hydrogel of the invention is implanted in a subject.

Among the above listed polymeric particles, poly(lactic-co-glycolic) acid (PLGA) particles are particularly preferred in the context of the present invention, most preferably PLGA nanoparticles. PLGA is indeed an attractive polymer, as it is biodegradable, biocompatible, exhibits a low toxicity, can be easily tailored, protects drugs from degradation, provides a sustained drug release, and has received the approval by the Food and Drug Administration (FDA) and European Medicine Agency (EMA) in drug delivery systems. PLGA is more particularly made of two copolymers of glycolide and lactide, of which the ratio may vary thereby providing different forms of PLGA (e.g. PLGA 70:30 identifies a copolymer whose composition is 70% lactic acid and 30% glycolic acid), and is capable to degrade following exposure to water, such as the aqueous environment of the body, into two natural by-products of metabolism (i.e. into monomers of lactic acid and glycolic acid). Its degradation time depends upon its copolymers' ratio, the higher the content of glycolide units, the lower the time required for degradation. It is within the skill of the person in the art to adjust the ratio of the PLGA copolymers in order to control the enzyme release rate, and hence the glucose delivery. Accordingly, the PLGA copolymers ratio is preferably chosen between the ratios 85:15 and 50:50. Of particular interest is PLGA 50:50, which exhibits the fastest degradation time (about two months). The molecular weight of PLGA may additionally influence the release rate of a molecule of interest. It is within the skill of the person in the art to adjust this molecular weight of in order to achieve the desired rate of enzyme release and hence of glucose delivery. Accordingly, in a preferred embodiment of the invention, the PLGA particles molecular weight is comprised between 10 and 100 000 Da, preferably between 30 000 and 60 000 Da.

According to a preferred embodiment, the polymeric particles d) concentration in the hydrogel is ranging from about 0.5 mg/ml to about 10 mg/ml, more preferably from about 0.75 mg/ml to about 5 mg/ml, and even more preferably from about 1 mg/ml to about 3 mg/ml. One skilled in the art would nevertheless understand that the concentration in polymeric particles d) may vary in the above indicated ranges depending upon the nature of said particles.

All the polymers of the hydrogel described herein are either commercially available or can be chemically synthetized using methods well known in the art as mentioned above.

According to a more preferred embodiment, the hydrogel of the invention comprises:

a) a fibrin hydrogel;
b) starch entrapped in said fibrin hydrogel; and
c) an α-glucosidase entrapped in said fibrin hydrogel.

Even more preferably, said α-glucosidase c) is entrapped within polymeric particles d), such as nanoparticles, in said fibrin hydrogel. Preferred embodiments are as described above. In particular, said α-glucosidase c) is preferably entrapped within PLGA nanoparticles.

Particularly preferred final concentrations of components a) to c) and size parameter of component d) in the hydrogel of the invention are as follows.

The fibrin concentration is preferably ranging from about 2.5 mg/ml to about 90 mg/ml, more preferably from about 5 mg/ml to about 40 mg/ml, even more preferably from about 10 mg/mL to about 25 mg/ml, and most preferably is 18 mg/ml.

The starch concentration is preferably ranging from about 1% (w/v) to about 10% (w/v), more preferably from about 2% (w/v) to about 8% (w/v), even more preferably from about 3% (w/v) to about 7% (w/v), yet more preferably is 1%, 2%, 3% or 4% (w/v), and most preferably is 1% or 2% (w/v).

The α-glucosidase concentration is set to obtain an enzymatic activity preferably ranging from about $1.10^{-5}$ µmol·min$^{-1}$·mg$^{-1}$ to about $1.10^{-3}$ µmol·min$^{-1}$·mg$^{-1}$, more preferably from about $2.10^{-5}$ µmol·min$^{-1}$·mg$^{-1}$ to about $7.10^{-4}$ µmol·min$^{-1}$·mg$^{-1}$, even more preferably from about $5.10^{-5}$ µmol·min$^{-1}$·mg$^{-1}$ to about $5.10^{4}$ µmol·min$^{-1}$·mg$^{-1}$, and most preferably is $2.10^{-4}$ µmol·min$^{-1}$·mg$^{-1}$.

The PGLA nanoparticles concentration is preferably ranging from about 0.5 mg/ml to about 10 mg/ml, more preferably between about 0.75 mg/ml to about 5 mg/ml, even more preferably between about 1 mg/ml to about 3 mg/ml, and most preferably is 2 mg/ml.

Besides, the PGLA nanoparticles size is preferably ranging from about 1 nm to about 1000 nm, more preferably from about 35 nm to about 800 nm, even more preferably from about 65 nm to about 600 nm, and most preferably from about 100 nm to about 400 nm.

The above preferred parameters have been identified by the Inventors as the optimal parameters allowing the formation of a homogenous and substantially free of syneresis hydrogel, which releases glucose in a prolonged manner for at least two weeks. Unexpectedly, even though the above-mentioned concentration of starch is relatively elevated, this particular concentration does not prevent the solubilisation of starch and enables not only the formation of a homogenous mixed hydrogel with fibrin, but also to limit the diffusion of starch from said hydrogel.

It is within the skill of ordinary person in the art to select the concentration of each components a) to c) and/or size of component d) to be used in the present hydrogel among the above defined concentrations. In particular, the skilled person in the art will readily understand that the different concentration ranges of components a) to c) and/or size of component d) may be combined, as required, and that the optimal concentration/size of said components may vary depending upon the use of the hydrogel.

For illustrative purposes, in a preferred embodiment in which the hydrogel of the invention may more particularly be used for bone regeneration, said hydrogel comprises 18 mg/ml fibrin; 4% starch; and $2.10^{-4}$ $\mu mol \cdot min^{-1} \cdot mg^{-1}$ α-glucosidase activity, said enzyme being preferably entrapped within PGLA nanoparticles. More preferably, said PGLA nanoparticles size is ranging from about 100 nm to about 400 nm, and/or said PGLA nanoparticles concentration is 2 mg/ml.

As indicated above, these concentrations represent the final concentrations of each component within the hydrogel. That is to say, for example, that the starch final concentration set forth in weight/volume percentages represents the weight of starch (in g) based on a volume of 100 ml of hydrogel; while the α-glucosidase concentration is set to reach a $2.10^{-4}$ $\mu mol \cdot min^{-1} \cdot mg^{-1}$ α-glucosidase activity within the hydrogel.

Furthermore, the term "about" as used herein means that these concentrations can vary within a certain range depending on the margin of error allowed, which may be easily determined by one skilled in the art. Preferably, this margin of error is of 10%, and more preferably of 5%.

As previously mentioned, the Inventors have demonstrated that the hydrogel of the invention is capable to integrate biological material, and may therefore be used as a tissue regenerating scaffold which can be implanted in a subject in need thereof. In particular, thanks to the beneficial properties of glucose delivered from such hydrogel, the survival and proper functionality of the implanted biological material and of its surrounding tissue and cells within the subject can be considerably improved.

Accordingly, in a further advantageous embodiment of the present invention, the hydrogel of the invention can further comprise at least one biological material. In other words, said biological material is entrapped in the hydrogel of the invention.

By "biological material", it is meant herein organic material that can have a biological activity and that is normally used by a living organism for generation or maintenance of life. In the context of the invention said material is preferably made of cells, tissue or stroma, which can either be natural, synthetic or engineered in vitro. Should the hydrogel of the invention comprising said biological material be used for implantation purposes in a subject, said biological material may be of homologous (same species), heterologous (different species), autologous (same subject), or isogenic (identical twin) origin.

Thus, according to a preferred embodiment, said biological material is selected from the group consisting of cells, tissues, stromata, derivatives thereof, and combinations thereof. For example, cells may be selected, without limitation, from chondrocyte cell lines, primary chondrocytes, stem cells, such as hMSCs (human mesenchymal stem cells) or bone marrow-derived MSCs, induced pluripotent stem cells, embryonic stem cells, adipose tissue-derived stem cells, keratinocytes, fibroblasts, smooth muscle cells, endothelial cells, or neurons. Tissues may be selected, among others, from bone tissue, cartilage, skin, cardiovascular tissue, smooth muscle, adipose tissue or nerve. Stromal vascular fraction (SVF) of adipose tissue is a further example of biological material suitable in the context of the present invention; it can notably contain preadipocytes, mesenchymal stem cells (MSC), endothelial progenitor cell, T cells, B cells, mast cells as well as adipose tissue macrophages. Cell or tissue derivatives may also be used such as rapid prototyped scaffolds (based on calcium phosphate or carbonate, artificial or synthetic polymers) (Yang et al., 2002), bone or cartilage substitutes (e.g. demineralized bone matrix, ceramics such as hydroxyapatite, tricalcium phosphate, coral, bioactive glasses, combinations thereof, etc), skin substitutes (e.g. Biobrane®, Transcyte®, Integra®, Alloderm®, Apligraf®, Dermagraf® to name a few, which may are commercialized, among other by Smith & Nephew, Integra, LifeCell, Apligraf, and Dermagraft), cardiovascular tissue substitutes (Zimmerman et al., 2003; Neal R. A. et al., 2012; Lundberg et al., 2013; Li et al., 2013; Fernandez et al., 2014), smooth muscle substitutes, or nerve substitutes (Konofaos et al., 2013).

Once generated, the hydrogel of the present invention can be used in a medical device, which may be administered to a patient in need thereof. In particular, as mentioned above, the hydrogel of the invention can be integrated in such device, in order to deliver glucose to a patient who is likely to benefit from its pro-angiogenic and pro-survival properties.

Therefore, it is another aspect of the present invention to provide a medical device, comprising the hydrogel according to the invention and optionally a pharmaceutically acceptable excipient.

As used herein, the term a "pharmaceutically acceptable excipient" means an inactive or inert, and therefore non-toxic, component, as it is has no pharmacological action, which can be used to improve properties of a composition, such as shelf-life, retention time at the application site, consumer acceptance, etc. It includes, without limitation, surfactants (cationic, anionic, or neutral); surface stabilizers; other enhancers, such as preservatives, wetting or emulsifying agents; solvents; buffers; salt solutions; dispersion medium; isotonic and absorption delaying agents, and the like; that are physiologically compatible.

The medical device according to the invention may further comprise at least one active agent, such as a therapeutic agent. For example, a suitable active agent according to the invention may be selected from the group consisting of, but not limited to: anti-apoptotic molecules, such as statins, insulin, B-cell lymphoma 2 (BCL-2), or stromal cell-derived factor 1 (SDF-1); growth factors and cytokines, such as epidermal (EGF), hepatocyte (HGF), fibroblast (FGF) or vascular endothelial (VEGF) Growth Factors, insulin-like growth factor (IGF), transforming growth factor-β (TGF-β), or bone morphogenetic proteins (BMPs); antibiotics, such as antibiotics belonging to the class of aminoglycosides, ansamycins, carbapenems, cephalosporins, glycopeptides, lincosamides, lipopeptides, macrolides, monobactams, nitrofurans, oxazolidonones, penicillins, polypeptides, quinolones, sulfanomides, or tetracyclines, etc; antiseptics, such as alcohols, quaternary ammonium compounds, boric acid, brilland green, chlorhexidine gluconate, or hydrogen peroxide; blood coagulation factors, such as fibrinogen, prothrombin, tissue factor, calcium, proaccelerin factor, Factor VI, proconvertin, antihemophilic factor, Christmas factor, Stuart-Prower factor, plasma thromboplastin antecedent, Hageman factor, and fibrin-stabilizing factor; oxygen carriers, such as perfluorocarbons (PFC), or recombinant or synthetic haemoglobin; anti-inflammatory agents, such as steroidal anti-inflammatory drugs (e.g. glucocorticoids), non-steroidal anti-inflammatory drugs (NSAID, e.g. aspirin, ibuprofen, or naproxen), or immune selective anti-inflammatory derivatives (ImSAIDs); and combinations thereof.

Such active agents may notably be particularly useful should the hydrogel of the invention be implanted in a subject in need thereof, or be used in a bandage or patch to heal wounds. Accordingly, in a preferred embodiment of the invention, said device comprising the hydrogel of the invention is a patch or bandage. Alternatively, in another preferred embodiment, said device comprising to the hydrogel of the invention is an implant.

As mentioned above, the hydrogel of the invention, or the medical device comprising said hydrogel, may be used in medical applications, which can benefit from the pro-angiogenic and/or pro-survival properties of the glucose released from said hydrogel. Angiogenesis is indeed known to facilitate not only the healing of injured skin, but also the growth of hair and fat tissue, nerve regeneration, as well as muscle and bone repair. Pro-survival properties of glucose may also help to combat oxidative stress, which is thought to be involved in a number of pathologies and traumas (cancer, lichen, tissue injury, etc.) and may hinder the success of a tissue or cell transplantation.

Thus, in another aspect, the invention provides a hydrogel, or a medical device as described above, for use as a medicament. Preferred embodiments as described above apply mutatis mutandis.

In particular, the hydrogel or medical device according to the invention allows the controlled release glucose at a rate which can improve symptoms or a condition. For example, said glucose may be delivered in a therapeutically effective amount sufficient to promote wound healing and/or facilitate tissue regeneration, depending upon the specific medical or cosmetic application. (e.g. treatment of a skin lesion, repair of a bone fracture, treatment of bone loss or ischemia, soft tissue filing such as wrinkles, etc.). It is within the skill of the person in the art to determine the desired therapeutic amount of glucose to deliver by routine methods in the art, e.g. by performing a dose-response experiment with varying doses administered to target cells or animals.

Accordingly, the invention preferably relates to the hydrogel or medical device of the invention, for use in a method of tissue regeneration in a subject in need thereof, such as in a method of bone, cartilage, skin, cardiovascular tissue, smooth muscle, or adipose tissue regeneration. More precisely, the present invention relates to the hydrogel or medical device of the invention, for use as a tissue regenerating medicament, such as a tissue graft. By "tissue regeneration", it is meant herein the regeneration of one or several tissues constituting the living body of a subject, such as the tissues exemplified above.

Still, preferably, the invention also relates to the hydrogel or medical device of the invention, for use in the treatment of a skin lesion in a subject in need thereof. More precisely, the present invention relates to the use of the hydrogel or medical device of the invention for manufacturing a medicament to treat a skin lesion. In other words, the invention relates to a method for treating a skin lesion in a subject in need thereof, comprising administering the hydrogel or medical device of the invention of the invention, to a subject in need thereof. The term "skin lesion" as used herein encompasses skin redness or soreness, dermatologically irritated skin, blisters and open wounds, burns, abscess and skin ulcer.

Yet, preferably, the invention further relates to the hydrogel or medical device of the invention, for use in the promotion of bone repair and/or in the treatment of bone loss. More precisely, the present invention relates to the use of the hydrogel or medical device of the invention for manufacturing a medicament to promote bone repair and/or treat bone loss. In other words, the invention relates to a method for promoting bone repair and/or treating bone loss in a subject in need thereof, comprising administering the hydrogel or medical device of the invention of the invention, to a subject in need thereof. By "bone loss", it is meant any bone impairment, that can notably be characterized by a decrease in bone mass. Said loss can result for example from bone loss disorders such as osteoporosis or periodontitis. "Bone repair" may be required even in the absence of a decrease in bone mass, following for example a bone marrow puncture or limb-salvage surgery, or a trauma leading to a bone fracture.

Still, advantageously, the invention also relates to the hydrogel or medical device of the invention, for use in the treatment of ischemia in a subject in need thereof, preferably of a local ischemia. More precisely, the present invention relates to the use of the hydrogel or medical device of the invention for manufacturing a medicament to treat ischemia. In other words, the invention relates to a method for treating ischemia in a subject in need thereof, comprising administering the hydrogel or medical device of the invention, to a subject in need thereof. By "ischemia", it is more particularly meant hypoxia resulting from obstructed blood flow to an affected tissue. For treating a local ischemia, said hydrogel or medical device may preferably be administered to a region of ischemic tissue in said subject.

The term "treating, "treatment" or "treat" as used herein encompasses, among other, preventing, ameliorating, inhibiting, or curing a deficiency, dysfunction, disease, or other deleterious process, including those that interfere and/or result from a therapy.

Still, advantageously, the present invention relates to a cosmetic method to prevent or reduce wrinkles, comprising administering the hydrogel or device of the invention, to a subject in need thereof. In other words, the invention relates to the cosmetic use of the hydrogel or device of the invention to prevent or reduce wrinkles. In this context, the cosmetic method aims to prevent or reduce natural aging, and as such, the subject is a healthy subject (i.e. non diseased).

Methods for administering to individuals the hydrogel or medical device according to the invention are well known to those skilled in the art. Such methods include, but are not limited to, inoculation or injection or implantation (e.g., intra-muscular, subcutaneous, intra-articular, etc.), or topical application (e.g., on skin areas such as wounds, burns, etc.). The method of administration will depend upon the desired application. Preferred methods for administering said hydrogel or medical device are injection or implantation, more preferably injection. A topical application can nevertheless be preferably chosen to treat for example a skin lesion.

The term "subject" refers throughout the specification to a human being or an animal, preferably to a human being.

In another aspect, the present invention relates to a method for preparing the hydrogel of the invention, comprising the step of mixing:
- a) a water-soluble gellable monomer or polymer;
- b) a glucose polymer; and
- c) at least one enzyme capable of hydrolysing the glucose polymer b) into glucose.

Preferred embodiments are as described above.

In particular, the above method may advantageously require the mixing of components a) to c), and of at least one biological material and/or at least one active agent as defined above.

By "gellable monomer or polymer", it is meant herein a monomer or a polymer capable of forming a network leading to a sol/gel phase transition, i.e. turning from a liquid solution to a solid gel. Such network formation (i.e. gelification) can be carried out by methods well-known in the art, which will vary depending on the nature of the monomer/polymer (De Gennes, 1979; Papon et al. (2006)). For example, gelification of said monomer/polymer may be carried out by modifying the temperature, by adding a saline solution (e.g. a solution containing calcium or barium ions), by modifying the pH or by crosslinking.

Such monomer/polymer may thus be qualified as "thermally gellable", if it is capable to form a gel following a temperature treatment, such as a decrease or increase in temperature. Examples of such polymer include, without limitation, gelatin, soybean proteins, ovalbumin, collagen, and carrageenan.

Alternatively, said monomer/polymer may be referred as "chemically gellable", if is capable to form a gel via a chemical reaction, for example, with metal cations which cause crosslinking (e.g. casein, or alginate), by modification of the pH (e.g. soybean proteins), by enzyme modification (e.g. alginate by using alginate epimerase; pectin by using pectine methylesterase; fibrinogen by using thrombin; or the use of chymosin-pepsin) or by crosslinking (e.g. by using glutardialdehyde, by using EDC/NHS, or by using Tgase, lysyl oxidase).

As indicated above, fibrin is a particularly preferred protein polymer a) of the hydrogel of the invention. Fibrin can be prepared by addition of thrombin to a solution of fibrinogen: in order to so, thrombin cleaves the N-Terminus of the fibrinogen alpha and beta chains into fibrinopeptide A and B, respectively. The resulting fibrin monomers subsequently polymerize end to end to form protofibrils, which in turn associate laterally to form fibrin fibers. In a final step, the fibrin fibers associate to form a fibrin gel. Accordingly, in this preferred embodiment of the invention, the water-soluble gellable monomer a) is advantageously fibrinogen.

Hence, according to a preferred embodiment, the method for preparing the hydrogel of the invention further comprises a step of gellifying the water-soluble gellable monomer or polymer. Still, advantageously, the above method further comprises the step of separately solubilizing the glucose polymer b) prior to mixing the components a) to c). In particular, should the glucose polymer b) be starch, a solubilization of starch is carried out at about 90° C., followed by autoclaving at about 122° C., 1 Pa (atmospheric pressure). Such conditions may notably be necessary if starch is present in an elevated concentration in the hydrogel, as described above, in order to obtain a homogeneous gel.

Besides, the quantity of each component can be easily determined by one skilled in the art based on the indications provided above, such as the preferred final concentrations of the invention.

Still, advantageously, the above method may further comprise the step of encapsulating the enzyme c) into polymeric particles as defined above, prior to mixing the components a) to c), by using a number of techniques well-known in the art. The choice of a particular technique usually depends on properties of the selected polymers, the characteristics of the enzyme to be delivered, and the desired release profile. For a detailed review of production methods, one skilled in the art may refer to Sinha et al. (2003) and Soppimath et al. (2001).

One skilled in the art would readily understand that the mixing of the above components is preferably carried out in experimental conditions (temperature, pH) which will not alter the activity of enzyme c) or denature its structure. It shall be further understood that the hydrogel may preferably be prepared in sterile conditions should it need be used in vivo, e.g. implanted in a subject in need thereof.

Besides, as indicated above, it is within the skill of the person in the art to determine the experimental conditions to prepare the hydrogel of the invention, in order to release glucose at a suitable or desirable rate.

Complete details for preparing a hydrogel made of fibrin, starch and α-glucosidase entrapped within nanoparticles are provided in the Examples described further below.

In order to prepare the hydrogel of the invention, it can be useful to provide a kit comprising the components of the gel. Accordingly, in another aspect, the present invention relates to a kit for use in the method described above, comprising:
- a) a water-soluble gellable monomer or polymer;
- b) a glucose polymer;
- c) at least one enzyme capable of hydrolysing the glucose polymer b) into molecules of glucose; and
- d) optionally, instructions for performing said method.

Preferred embodiments are as described above. In particular, the above kit may further comprise a polymer suitable to encapsulate said enzyme c) into polymeric particles, and/or at least one biological material and/or at least one active agent, as defined above.

The above kit may also further comprise a compound that can promote or facilitate gelification of the water-soluble gellable monomer or polymer, as defined above.

As used herein, the term "instructions" refers to a publication, a recording, a diagram, or any other medium of expression which can be used to communicate how to prepare the hydrogel of the invention. Said instructions can, for example, be affixed to a container which contains said kit.

The present invention will be better understood in the light of the following detailed description of experiments, including examples. Nevertheless, the skilled artisan will appreciate that this detailed description is not limitative and that various modifications, substitutions, omissions, and changes may be made without departing from the scope of the invention.

Various assays were carried out to entrap directly the glucose in the hydrogels, and facing the impossibility to keep directly the glucose into the gel phase, different coral scaffolds based polyelectrolytes systems were tested as potential reservoirs.

Figure 1:
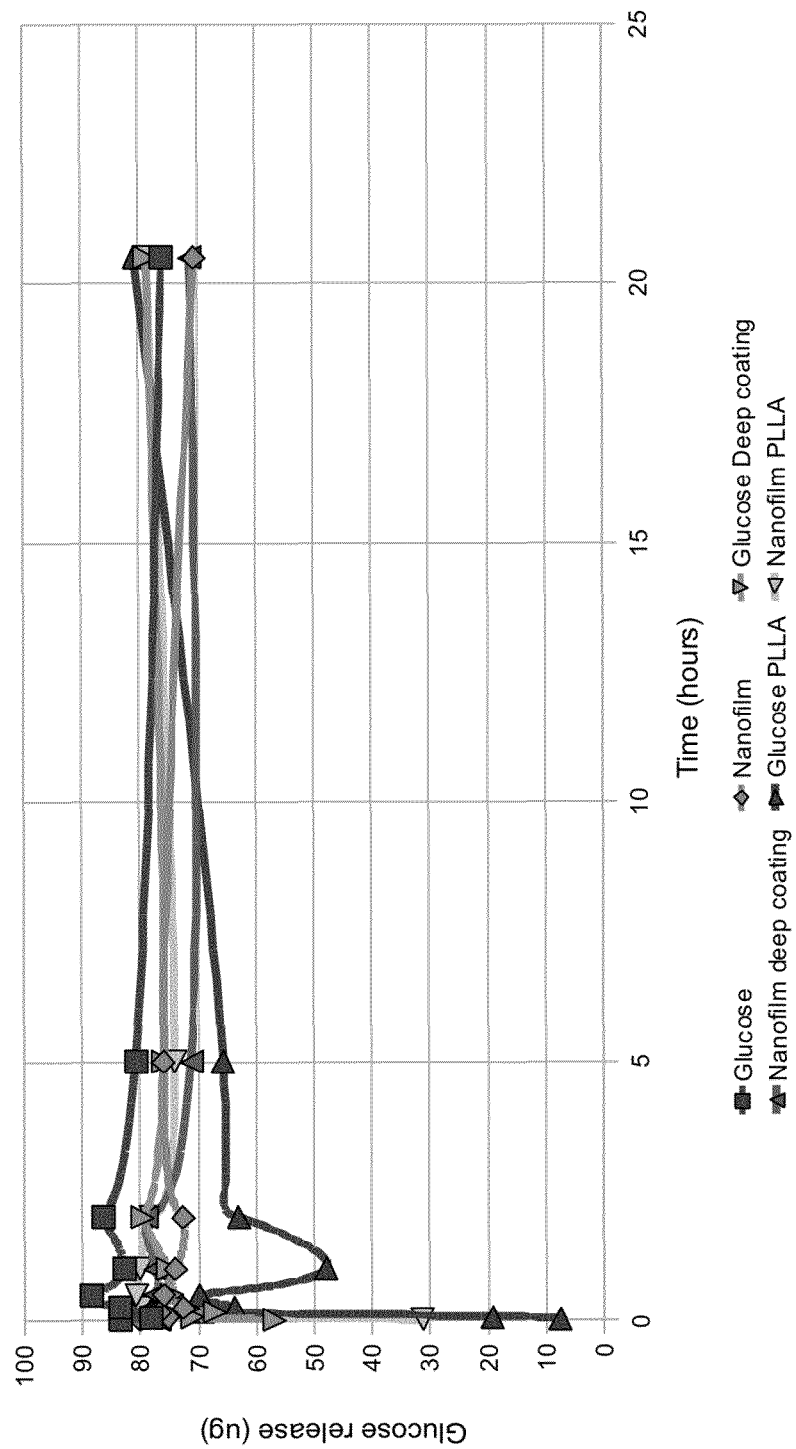
FIG. 1 shows the different strategies tried to limit the burst release of the glucose entrapped in the hydrogels and to subsequently control the kinetic of the delivery of glucose.

Basically, corals (at pH 6.0) were immersed during a couple of hours in a glucose solution at 20 g/L (sample referred as "glucose" on FIG. 1). Then, different post treatments were performed in order to attempt limiting the glucose delivery from the coral scaffolds:

i) a film of PLLA was deposited around the corals via deep-coating or evaporation (sample referred on FIG. 1 as "glucose deep coating" and "glucose PLLA", respectively);

ii) a 20 layers thinfilm consisting of PLL and PGA deposit thanks to the layer-by-layer strategy was made around the corals incubated with glucose (sample referred as "nanofilm" on FIG. 1);

iii) a 20 layers thinfilm consisting of L-B-L PLL/PGA followed by a deeped or evaporated PLLA film (sample referred as "nanofilm deep coating" and "nanofilm PLLA", respectively).

Figure 2:
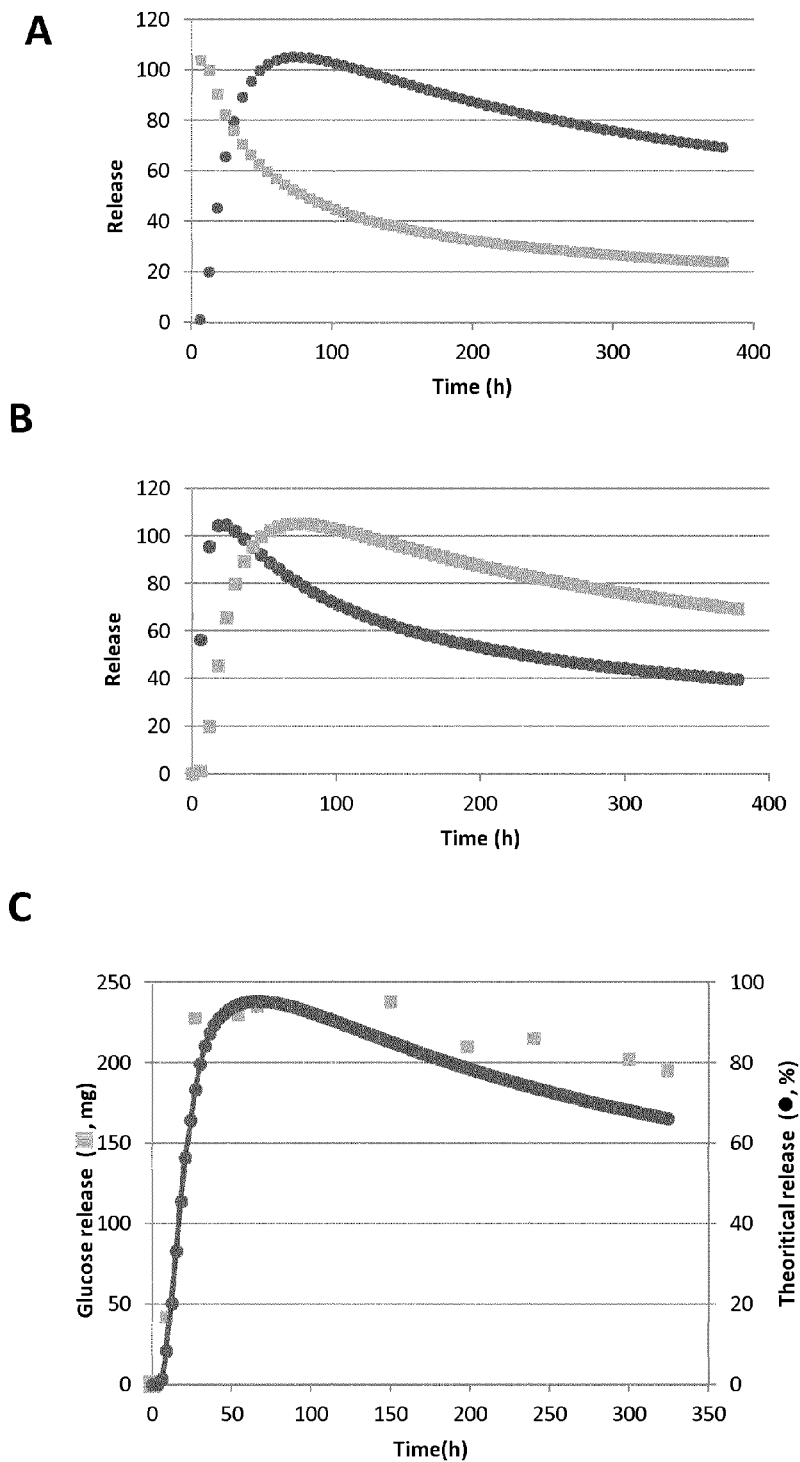

FIG. 2 shows that the hydrogels of the invention, comprising a glucose polymer, allows a constant release of a high quantity of glucose for more than 350 hours.

(A) The addition of a glucose polymer increased the viscosity of the inner hydrogel and allowed both the delay of the glucose burst and the stabilisation of the level of glucose released. Hydrogel containing glucose without glucose polymer (squares) exhibited an almost immediate burst release whereas glucose polymer addition to the previous hydrogel (circles) allowed a delayed delivery and a higher and longer glucose release.

(B) Comparative release kinetics of glucose based on the selected starch. The delay of glucose delivery and the concentration of glucose released were higher with wheat starch (squares) than with corn starch (circles), as glucose polymers respectively.

(C) Glucose delivery from 4% wheat starch as a function of time with the enzyme directly entrapped in the gel. Comparison of theoretical and experimental release. Results for the mathematical model (circles) were in accordance with the experimental results (squares).

Figure 3:
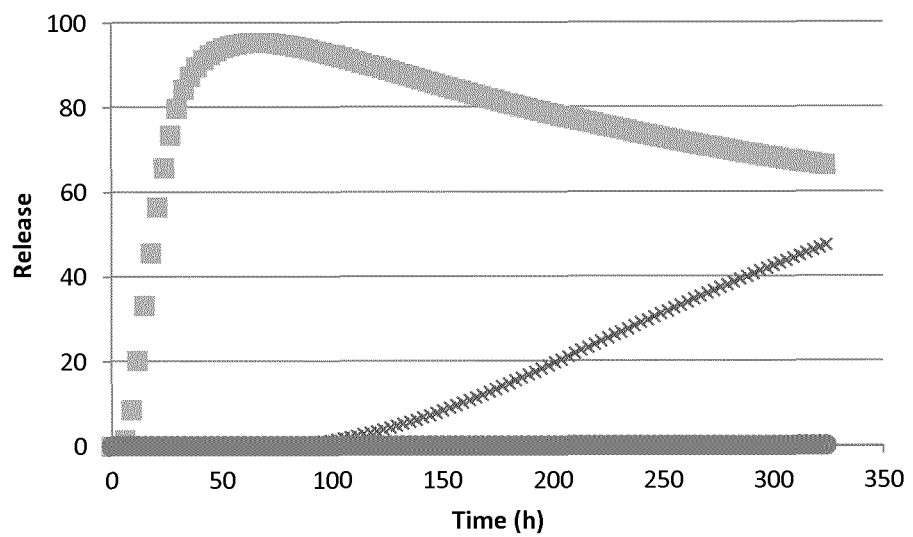

FIG. 3 shows that the use of nanoparticules encapsulating an enzyme capable of hydrolysing a glucose polymer into glucose (herein, α-amyloglucosidase) allows a gradual and constant delivery of enzyme and reduce its release out of the hydrogel, in order to prolonge the rate of glucose delivery (squares). Indeed, without entrappement of the enzyme within the nanoparticules, the enzyme started to be released out of the hydrogel (cross) on day 4, whereas the use of nanoparticules encapsulating the enzyme prevented its release (circles).

Figure 4A:
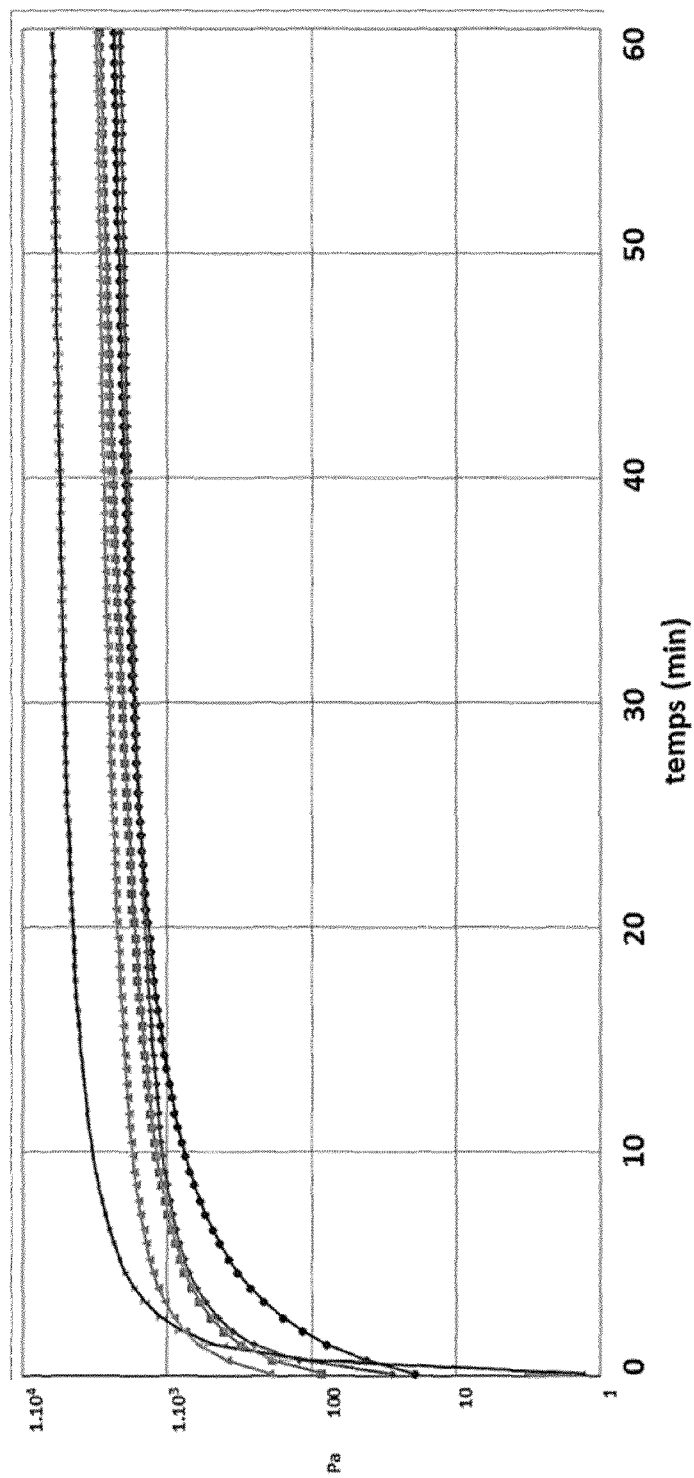
Figure 4B:
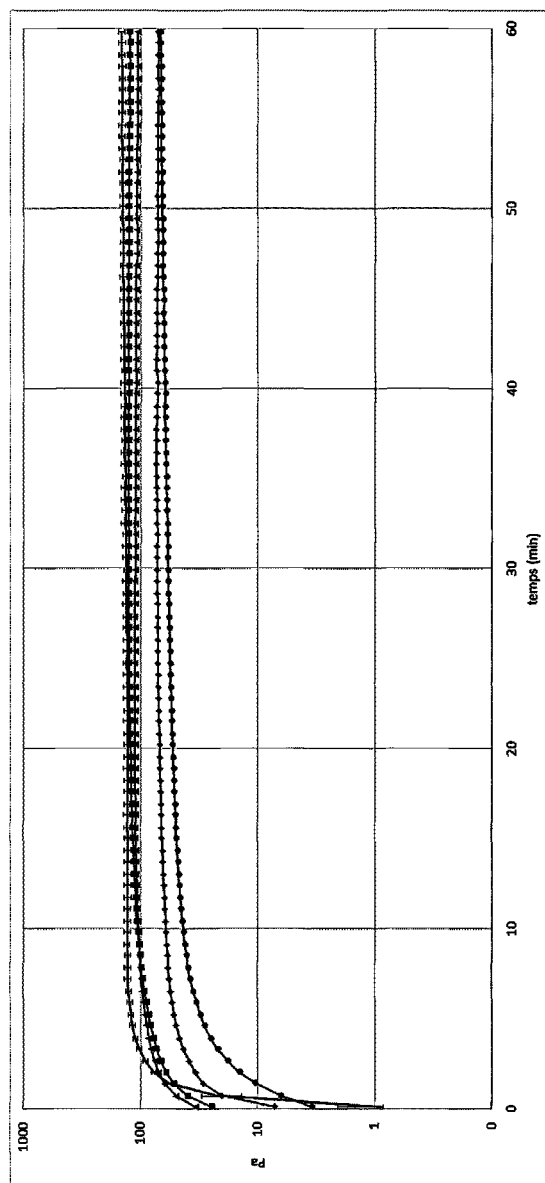

FIG. 4 shows that corn and wheat starchs have the smallest impact on rheologic properties of the hydrogels by comparison to rice and potato starch, based on rheology measurements of various hydrogels comprising said glucose polymers as a function of time. Storage modulus (FIG. 4A) and loss modulus (FIG. 4B) of hFb/starch materials for rice (diamonds), corn (squares), potato (circles) and wheat (triangles) at a 2% concentration (w/V). Storage modulus (black line—Figure A) and loss modulus (black line—Figure B) of a simple fibrin hydrogel was presented as a reference.

Figure 5:
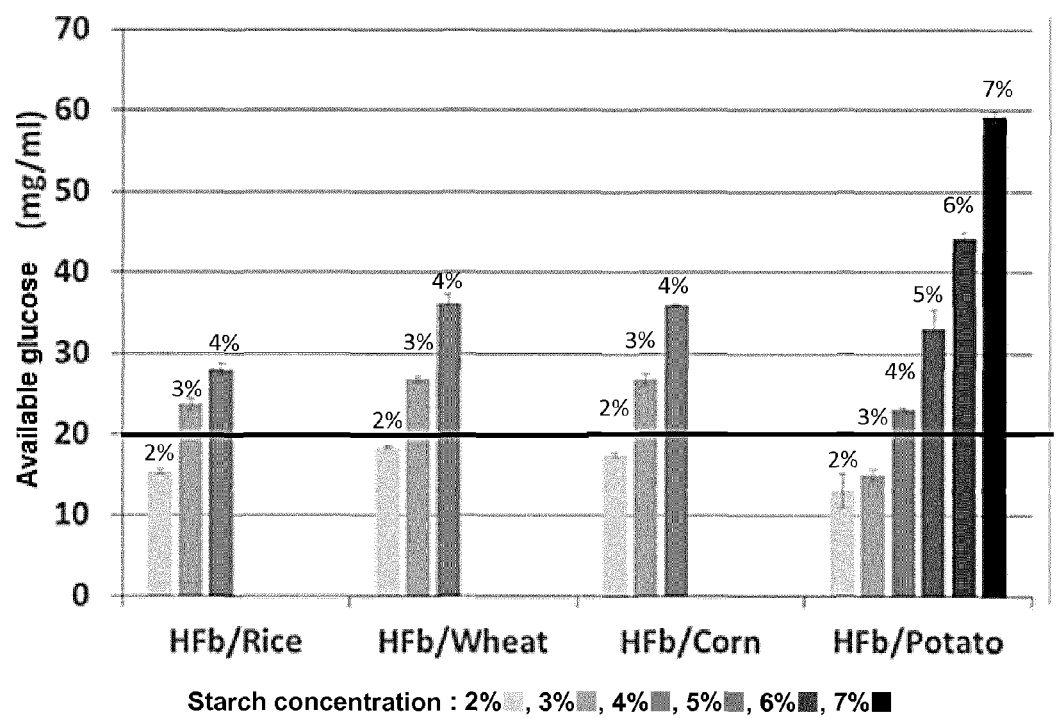

FIG. 5 shows that the hydrogels of the invention can retain high amount of glucose polymer. The available glucose concentration is presented herein for different starch concentrations originating from various sources entrapped into the hydrogel.

Figure 6:
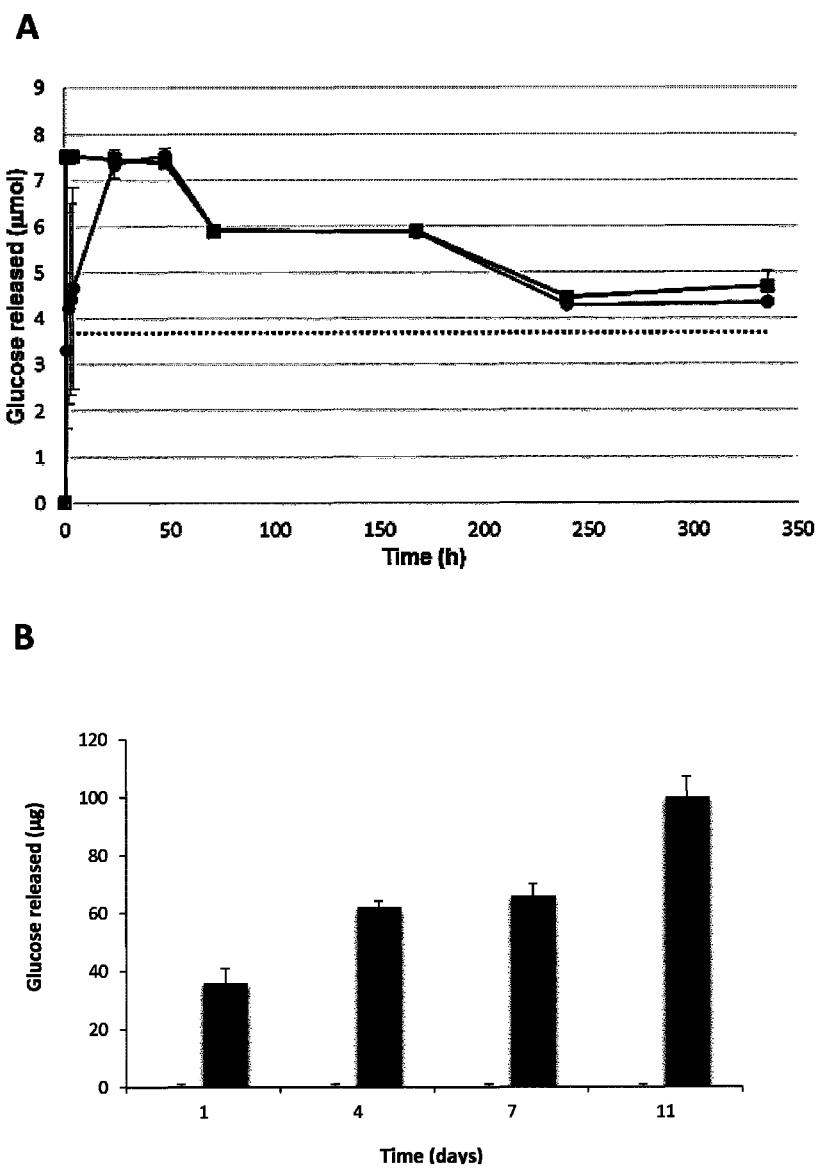

FIG. 6 shows that the hydrogels of the invention allow a constant release of glucose. A) over 350 hours (release of glucose from hFb/4% starch implant containing nanoparticles encapsulating α-amyloglucosidase as a function of time; Corn starch (squares), wheat starch (circles). The dotted line shows the required glucose level). B) over 260 hours (release of glucose from hFb/2% starch implant containing nanoparticles encapsulating α-amyloglucosidase as a function of time).

Figure 7:
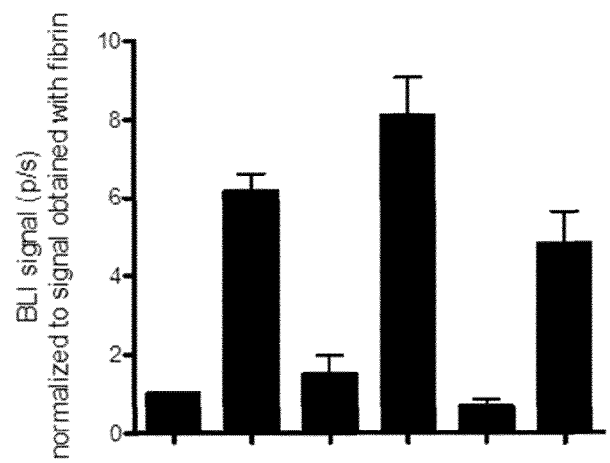
Figure 7:
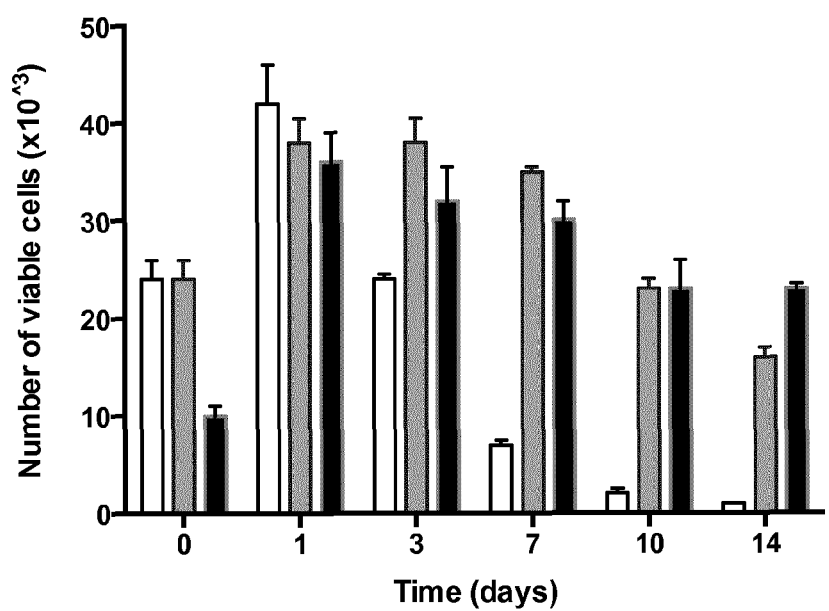
Figure 7:
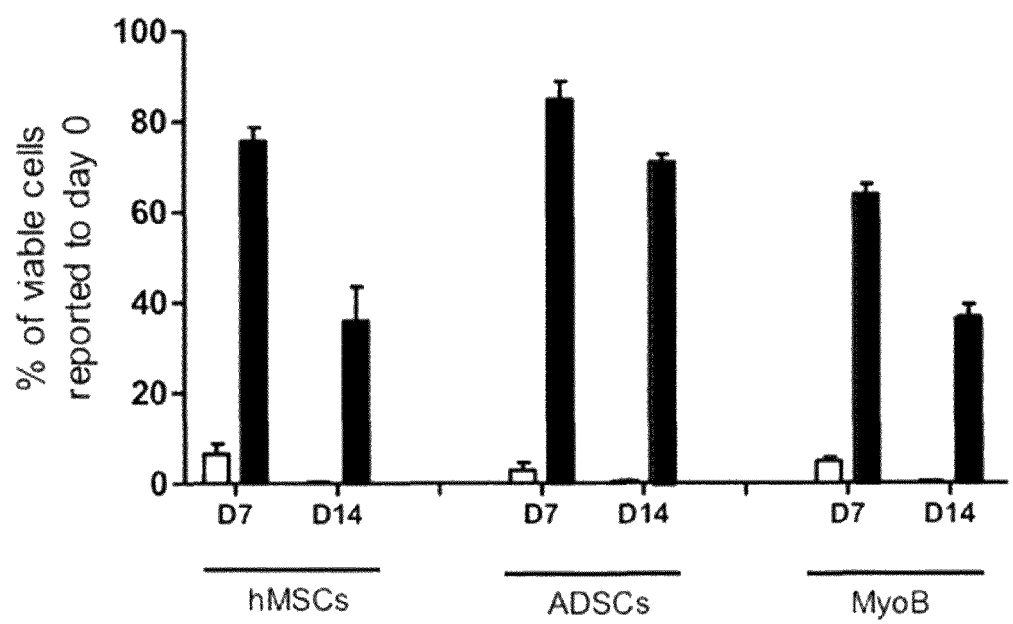

FIG. 7 shows that the hydrogels of the invention can be used to improve the survival of cells seeded into the hydrogel, particularly in in vitro ischemic conditions. A) Hydrogels comprising hMSC, fibrin, heated starch, nanoparticles and an enzyme capable of hydrolysing starch allowed an improvement of the hMSC viability after 7 days in ischemic conditions by comparison to a hydrogel made solely out of fibrin. B) Hydrogels comprising hMSC, fibrin, heated starch, nanoparticles and an enzyme capable of hydrolyzing starch allowed an improvement of the hMSC viability by comparison to a hydrogel made solely out of fibrin or comprising glucose at a concentration of 5 g/L. C) Hydrogels comprising fibrin, heated starch, nanoparticles and an enzyme capable of hydrolysing starch allowed an improvement of the viability of hMSC but also myoblast and human adipose-derived stem cells (ADSC) after 14 days in ischemic conditions by comparison to a hydrogel made solely out of fibrin.

Figure 8:
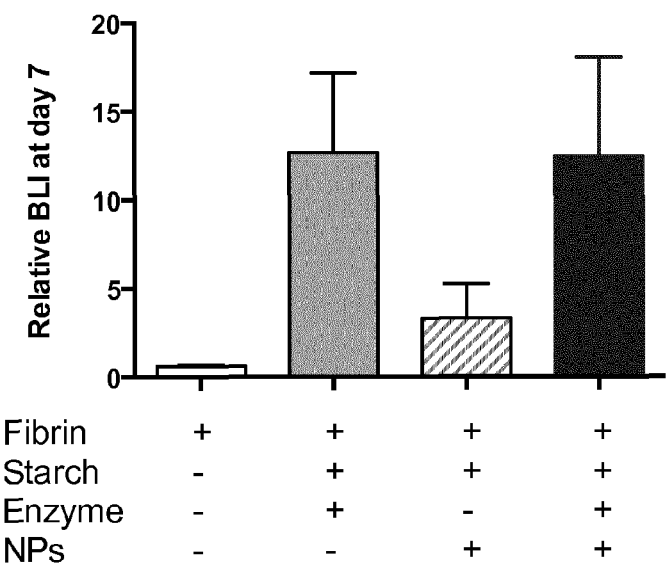
Figure 8:
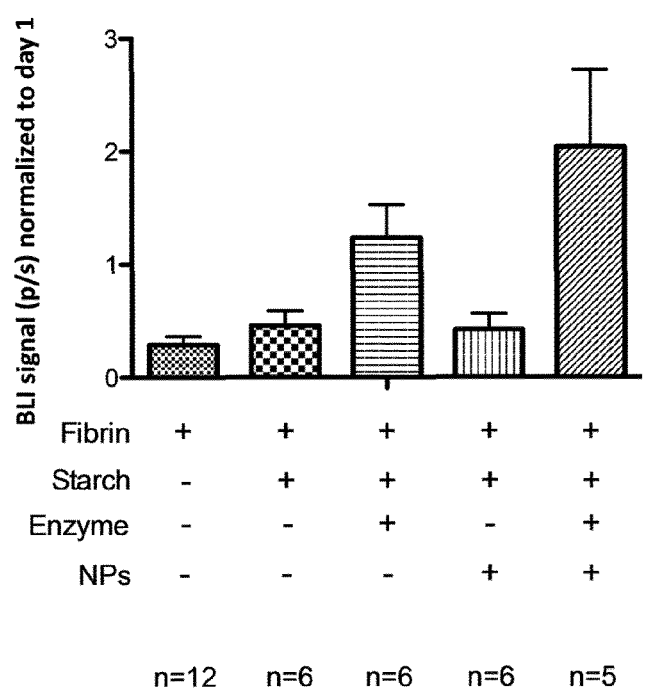
Figure 8:
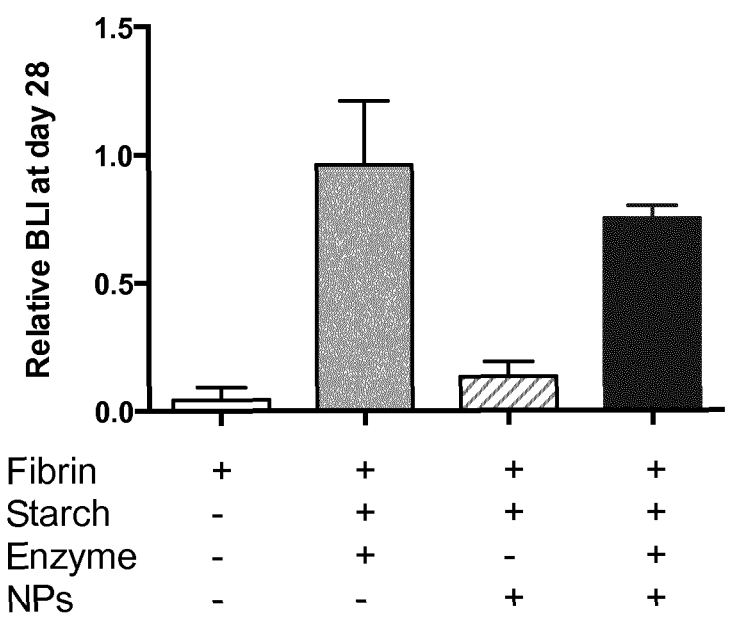

FIG. 8 shows that the hydrogels of the invention improve the survival of biological material loaded within the hydrogel, particularly in in vivo ischemic conditions. Hydrogels comprising fibrin, enzyme, heat starch and/or nanoparticles/enzyme capable of hydrolysing starch were implanted in mice and Bioluminescent Intensity produced by hCSM were measured at day 7 (A), day 14 (B) and day 28 (C).

Figure 9:
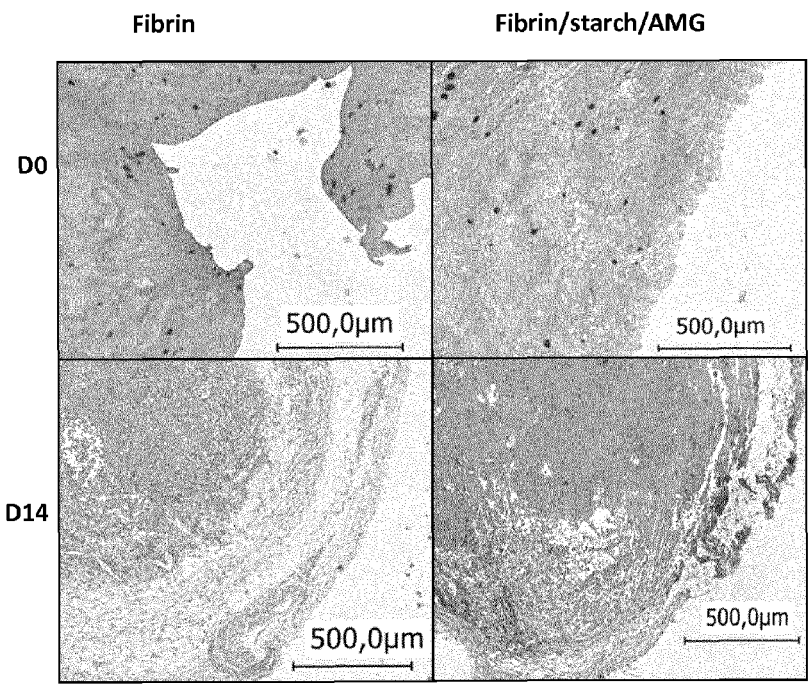
Figure 9:
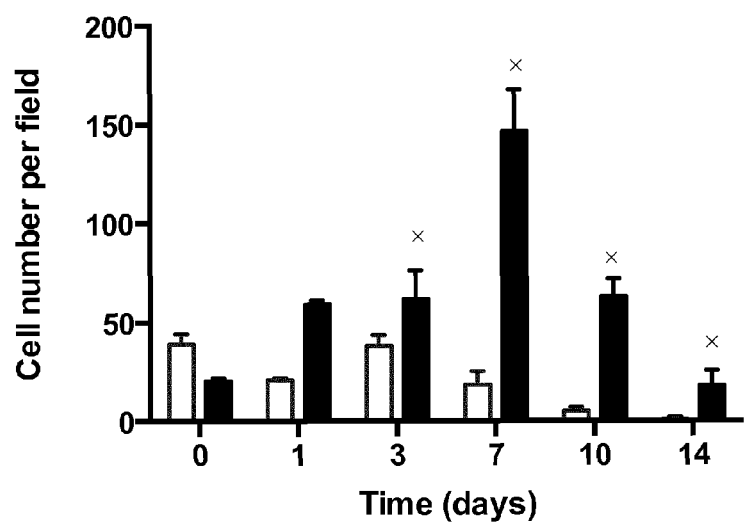

FIG. 9 shows that the hydrogels of the invention improve the survival of biological material (hMSCs) loaded within the hydrogel in in vivo ischemic conditions. (A) Representative micrographs of hydrogels containing hMSCs for up to 14 days. (B) quantification of viable hMSCs in hydrogels during 14 days with hydrogels containing Fibrin/starch/AMG (black) in comparison to hydrogels containing Fibrin (white). x: comparison between hydrogels containing Fibrin/starch/AMG and hydrogels containing Fibrin with a two way ANOVA analysis (p<0.05).

Figure 10:
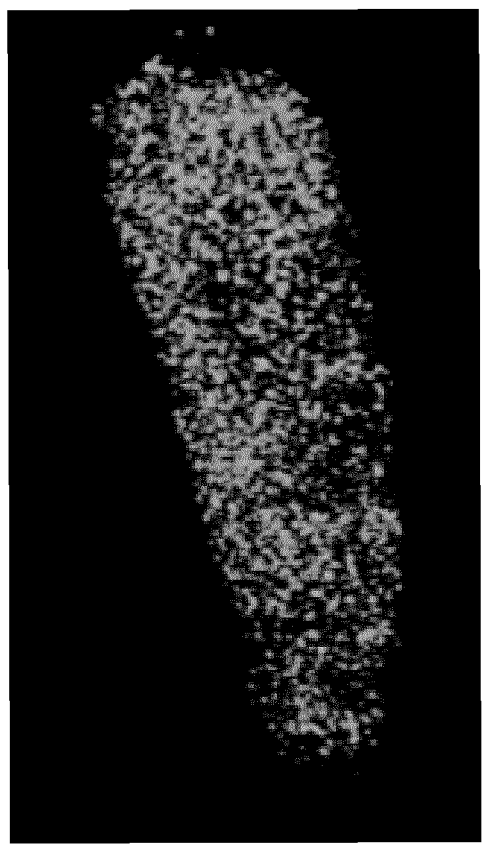

FIG. 10 shows the integration of coral particles inside hydrogels.

Figure 11:
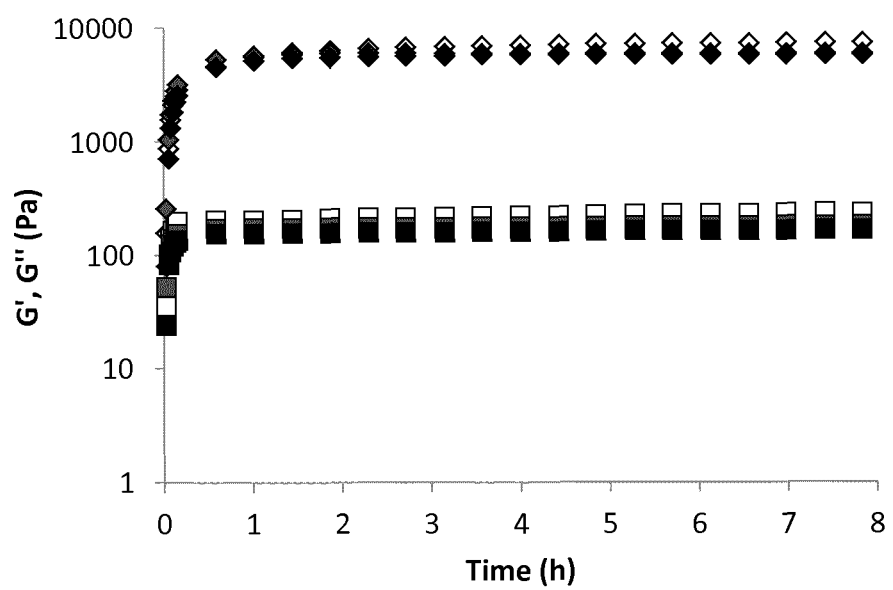

FIG. 11 shows the stability of the kit comprising the components of the gel, after long term storage (up to 21 days). The mechanical properties (storage and loss moduli G' and G") are identical at D0, D7 or D21 storage.

EXAMPLES

1. Material and Methods 1.1. Solubilization of Fibrin

Under laminar flow hood, fibrinogen was solubilized at a 50 mg·ml$^{-1}$ concentration in Hepes buffer 10 mM pH 7.4 at 37° C. Then, the solution was incubated during 3 h at 37° C. without any shacking to complete solubilisation of the protein.

1.2. Solubilization of Thrombin

Under PSM, Thrombin was solubilized at a 100 u·ml$^{-1}$ concentration in Hepes buffer 10 mM pH 6.5 with 0.1% (w/v) BSA, at 37° C. The resulting solution was either stored at 20° C. at this concentration, or diluted at 20 u·ml$^{-1}$.

1.3. Solubilization of Starch

A suspension of 8% (w/v) starch, 300 mM NaCl and 40 mM CaCl$_2$ was prepared in Hepes buffer 10 mM pH 7.4. The solubilization of starch was achieved by incubating this solution at 90° C. during 2 h with stirring followed by autoclaving (121° C., 1 Pa). The starch solution was then cooled down at room temperature overnight.

1.4. Nanoparticles Synthesis

Nanoparticles were prepared using the double emulsion technique. Briefly, poly(lactic-co-glycolic) acid (PLGA) was dissolved in dichloromethane at 0.5% (w/v), covered and incubated for 1 h at room temperature. A concentrated α-amyloglucosidase solution (glucan 1,4 α-glucosidase, EC: 3.2.1.3) was added to the PLGA solution and was submitted three times to a 10 s sonication. 5% (w/v) polyvinyl alcohol (PVA) was previously prepared by dissolving PVA in Hepes 10 mM pH 7.4. The solution was heated under stirring for 2 h at 90° C. and cooled down to room temperature. This PVA solution was added to the first emulsion with a 2:1 volume ratio PVA/first emulsion, and then submitted three times to a 10 s sonication. This second emulsion was poured into a 0.3% (w/v) PVA solution with a 50:3 volume ratio PVA/second emulsion. Then to evaporate the dichloromethane, the solution was placed under stirring for 3 h at room temperature. The resulting nanoparticles were centrifuged at 12,000 rpm for 8 min and resuspended in Hepes 10 mM pH 7.4 three times. After flash freezing and lyophilisation, dried nanoparticles were collected and resuspended in deionized water.

1.5. Gelation Procedure

The starch solution was firstly heated during 2 h at 90° C. with stirring, and the fibrinogen and thrombin solutions were heated for 15 minutes at 37° C., while the α-amyloglucosidase solution was kept at room temperature.

The starch solution was mixed with an appropriate volume of Hepes buffer 10 mM pH 7.4, based on the final volume. Then, all solutions were cooled down at room temperature before adding fibrinogen (50 mg·ml$^{-1}$) and an appropriate volume of α-amyloglucosidase which was either free or entrapped in nanoparticles. The polymerization of the hydrogel was subsequently initiated by introducing thrombin at a 20 u·ml$^{-1}$ concentration in the mix. The final concentration of each component of the gel was: 4% (w/v) starch, 0.5% (w/v) fibrinogen and 2 u·ml$^{-1}$ thrombin, while the concentration of α-amyloglucosidase had to be adapted with the desired quantity of released of glucose. As soon as the thrombin was introduced, the mix was put in a teflon tubular mold which was sealed to avoid any drying. The polymerization was carried out during 1 h at 37° C. After polymerization, the hydrogel was removed from the mold with a needle and stored in Hepes buffer 10 mM pH 7.4.

1.6. In Vitro Analysis of Glucose "Production"

To study glucose release, the hydrogel was incubated in Hepes buffer 10 mM pH 7.4. A fraction or total volume of buffer was collected at different time points, and replaced by fresh Hepes buffer solution. Glucose concentration in collected fractions was determined using Glucose (GO) Assay Kit from Sigma (Product code GAGO-20). Briefly, released glucose was oxidized into gluconic acid and hydrogen peroxide by glucose oxidase. The produced hydrogen peroxide reacted with the reduced o-dianisidine in the presence of peroxidase to form oxidized o-dianisidine. The oxidized o-dianisidine then reacted with sulfuric acid to form a more stable pink colored product. The intensity of the pink color measured at 540 nm was proportional to the original glucose concentration. Glucose concentration was then determined using a standard curve made with a glucose standard solution.

1.7. Cells Cultures

Human mesenchymal stem cells (hMSCs) were isolated from bone marrow obtained as discarded tissue during routine bone surgery from 5 adult donors at the Lariboisiere Hospital Paris, France, according to the French bioethics laws These cells were isolated from each patient's bone marrow using a procedure adapted from literature reports, characterized, pooled at an equal ratio at passage 1, and were cultured in Alpha Minimum Essential Medium (αMEM; Dutscher, Brumath, France) under standard cell culture conditions, that is, a humidified 37° C., 5% $CO_2$, 95% air environment. At 80-85% confluence, the cells were trypsinized using trypsin-EDTA (Sigma) and passaged. Cells passages 4-5 were used for experiments. ADSCs were cultured in the same conditions, and specific media was used for myoblasts cultivation.

1.8. In Vivo Experiments

1.8.a) Isolation and Transduction of Human Mesenchymal Stem Cells (hMSCs)

Human mesenchymal stem cells (hMSCs) were isolated from the bone marrow samples of discarded tissue obtained during routine bone surgery at the Lariboisiere Hospital (Paris, France), as previously described (Friedenstein et al., 1987). hMSCs from 5 donors at passages 4-5 were pooled for the experiments described in the sections that follow. Each experiment was conducted in sextuplicate. For the in vivo evaluation of cell survival, hMSCs were genetically modified by rMLV-LTR-eGFP-luc retroviral vector that contains fused genes encoding for the firefly luciferase (Luc) and for the green fluorescent protein (GFP).

1.8.b) Preparation of a Hydrogel Containing hMSCs Cells

The hydrogel was prepared as described above the day before implantation, without adding thrombin, and subsequently mixed with. 3×10.$^5$ GFP-Luc hMSCs cells The thrombin was then added to this mix, which was then incubated for 1 h at 37° C. to allow polymerization. After removal from the mold, the cell-containing hydrogel was stored in a phosphate suffer solution (PBS).

Four different types of hydrogels were generated for in vivo studies, i.e. hydrogels containing
  (i) cells/fibrin (n=6),
  (ii) cells/starch/fibrin (n=6),
  (iii) cells/starch/fibrin/amyloglucosidase (n=6), and
  (iv) cells/starch/fibrin/amyloglucosidase encapsulated in nanoparticles (n=6).

1.8.c) Surgical Procedure hMScs survival was assessed in a mouse ectopic model (8-week-old male nu/nu mice; Janvier, St Berthevin, France). All animal procedures were performed in compliance with institutional published guidelines (Directive du Conseil 24.11.1986. 86/609/CEE).

Nude mice (nu/nu) (30 g body weight) were anaesthetized by an intraperitoneal injection of 1 mg/10 g kétamine (Ketalar®, ROCHE) and 0.1 mg/10 g xylazine (Rompun®, BAYER). Incisions (each 5 mm long) were made along the vertebral axis and separated subcutaneous pockets (in the thoracic and in the lumbar regions) were created by blunt dissection. The cell-containing hydrogels were then randomly implanted in the subcutaneous pockets of the mice, and skin closure was accomplished using interrupted Ethicon non-resorbable vicryl 3-0 sutures (Johnson and Johnson, Belgium).

1.8.d) In Vivo Cell Survival Assessment

Cell survival was assessed by bioluminescence imaging. Briefly, at day 1, 7 and 14 post-implantation, 0.1 ml of D-Luciferin (15 mg/mL in PBS) was locally injected at the implantation sites of each anesthetized (by inhaling isoflurane) mouse. Animals were then placed in the prone position inside the detection chamber of the bioluminescent imaging system (Ivis Lumina II®, Caliper Life Science) and the photons flux for the region of interest of each implant was quantified using the living Image® 3.1 software (Caliper Life Science).

1.8.e) Immunohistology

In addition to Bioluminescence assessment, viable human Mesenchymal Stem cells remaining in the hydrogels were detected using immunohistology, Briefly, at days 1, 3, 7, 10 and 14 post-implantation, hydrogels were collected, fixed in paraformaldehyde 4% and paraffin embedded. 5 μm thin sections were used for immunohistological analysis targeting β2-microglobuline, a specific marker of human cells (Dako kit, Envision). Hydrogels sections were microscopically analysed and the number of immuno-stained cells in each hydrogel was determined.

1.9. Mathematical Model for Measuring Glucose Release from the Hydrogel

The present model was based on a general solution of diffusion in liquid phases. This model was modified to integrate steric hindrance due to the gel network. It was based on the second Fick's law which considered both the kinetics (time, t) and space conditions (x) as follows:

$$\frac{\partial \phi}{\partial t} = D \frac{\partial^2 \phi}{\partial x^2}$$

The general solution for this equation in a three-dimensional model was:

$$n = \frac{n_0}{\sqrt{4 \cdot \pi \cdot D \cdot t}} \cdot e^{-\frac{x^2}{4 \cdot D \cdot t}}$$

where $n_0$ was the initial concentration of diffusing molecules of interest, D the diffusion coefficient of the diffusive molecule in the considered medium, x the diffusion distance, and n the molecules concentration at distance x and at instant t.

Calculations were carried out as follows:
the concentration of the diffusive molecule was normalized to 100 (adimensional value) to express results in %, so that $n_0$=100;
hydrodynamical radii were obtained from literature or experimentally determined (e.g. by dynamical light scattering);
diffusion coefficients were simply calculated using the Stokes-Einstein equation:

$$D = \frac{k_B T}{6\pi \eta r}$$

Where D was expressed in $m^2 \cdot s^{-1}$, $\kappa_B$ is the Bolzmann's constant, T the temperature in kelvin, η the viscosity in Pa·s., and r the dynamical radius in m;
an x value equal to 2.3 mm, the mean radius of the gel considered as a sphere, was used as the diffusion distance.

The presence of the gel network was taken into account to evaluate the viscosity of the liquid phase. A derivation from the Einstein equation relating the viscosity of a suspension of solid particles to the viscosity of the dispersion medium $\eta_s$ was considered:

$$\eta = \eta_s(1 + 2.5\varphi + 6.2\varphi^2)$$

where $\eta_s$ was the solvent viscosity (i.e. water viscosity of $10^{-3}$ Pa·s) in absence of starch and φ the solid volumic fraction. Here, φ was the fibrin concentration, 1.8%, considered as entirely engaged in the solid network.

The liquid phase viscosity varied with the nature and concentration of starch entrapped in the fibrin gel. Viscosity was the parameter modulating diffusional constraints. Hence, viscosity, η was measured by rheology for each type and concentration of starch used in the fibrin gels. Diffusion coefficients, D, were then calculated for each material from these data.

Besides, the average mesh size of the solid phase of the gel was evaluated from rheology data when the gel had reached a quasi-equilibrium point using the Maxwell model, assuming that the volume $\xi^3$ stored an elastic energy equal to $\kappa_B T$. Using a Gaussian repartition the relation became:

$$\xi^3 = \kappa_B T / G'$$

where ξ was the mesh size and G' the storage modulus expressed in Pa. For a G' value of $10^3$ Pa, an average mesh size of 16.2 nm was assumed. This value was used to evaluate the role of steric hindrance generated by the solid network on diffusion of large molecules. Hydrodynamical radii were: 0.43 nm for glucose, 7 nm for enzyme and 250 nm for nanoparticles. Ionic interaction might as well alter the diffusion this parameter was however omitted from the calculations as starch and glucose were uncharged.

1.10. Evaluation of Coral Distribution Inside the Hydrogel

A coral-containing hydrogel was prepared as described in the "gelation procedure" section described above (1.5). Briefly, the pre-heated starch solution was mixed with an appropriate volume of Hepes buffer 10 mM pH 7.4, based on the final volume. Then, all solutions were cooled down at room temperature before adding fibrinogen (50 mg·ml$^{-1}$). At that time, 400 mg/ml of coral particles (600-1000 micrometers in average) were added and gently mixed to the mix. The polymerization of the hydrogel was subsequently initiated by introducing thrombin at a 20 μ·ml$^{-1}$ concentration in the mix. The final concentration of each component of the gel was: 4% (w/v) starch, 0.5% (w/v) fibrinogen and 2 μ·ml$^{-1}$ thrombin and 400 mg/ml coral. As soon as the thrombin was introduced, the mix was put in a teflon tubular mold which was sealed to avoid any drying. The polymerization was carried out during 1 h at 37° C. After polymerization, the hydrogel was removed from the mold with a needle and imaged with a micro-scanner (Skyscan 1172, Bruker, France).

2. Results 2.1. Modelisation of Glucose Diffusion in a Hydrogel Containing Glucose or Starch Several strategies were pursued to attempt limiting the release of glucose directly entrapped in hydrogels and to subsequently control the kinetic of glucose delivery (FIG. 1). However, none of the different post-treatments performed, as described in the legend of FIG. 1 above, were successful in limiting the glucose delivery from the gel. Indeed, after few seconds, all treated gel had released from about 70 μg to 80 μg of glucose, and no more glucose was released afterwards. This experience was performed over a period of 20 hours, during which the supernatant was not renewed after each measure of glucose (by contrast, all further experiments were carried out on a longer timeline by renewing the supernatant after each measure of glucose). It can therefore be concluded that, whatever the system used, an efficient entrappment of glucose does not allow to control its delivery in a prolonged manner.

2.1.a) Glucose Directly Entrapped in the Gel at t=0

Modelisation of glucose diffusion as illustrated in FIG. 2 demonstrated that a constant delivery of glucose over a long period of time depended on its regular production in situ. This modelisation indeed showed that a regular in situ production of glucose was necessary in order to maintain constant its internal concentration, while an alternative solution consisting in introducing a large concentration of glucose at t=0 was not pertinent.

The following calculations were based on the former condition (in situ production of glucose=constant or pseudo-constant glucose concentration).

2.1.b) Impact of Starch on the Glucose Delivery Kinetic

As shown in FIG. 2A, the use of a hydrogel without starch which contained a fixed quantity of glucose led to the release of glucose released firstly into a large burst rapidly followed by a stabilization phase where the quantity of glucose delivered was far smaller.

By contrast, the use of a hydrogel containing starch as a glucose polymer (instead of pure glucose) increased not only the internal viscosity of the fibrin gel, but slowed down as well the gel viscosity variations (FIG. 2A). This led to a delayed delivery of glucose as well as to a higher and longer release of glucose. This hydrogel further displayed a homogeneous structure, a lack of syneresis and good mechanical properties; the presence of starch did not affect the gelification time of fibrin, and did not alter the fibrin network properties.

Those results therefore showed that the addition of starch as a source of polymerized glucose in the hydrogel was crucial, notably for its viscosigen property. The starch to be selected should therefore be able to mechanically support the enzymatic hydrolysis over time, as confirmed by the experimental results displayed on FIGS. 2B and 2C. Indeed, wheat starch displayed a higher viscosity compared to corn starch and lead to a more constant glucose delivery over time (FIG. 2B).

2.1.c) Enzyme Diffusion

Modelisation of the results obtained with a hydrogel containing a non encapsulated enzyme capable of hydrolysing a glucose polymer into glucose (herein α-amyloglucosidase) showed that said enzyme was released from the gel after 4 days (FIG. 3). By contrast, the enzyme encapsulation into nanoparticles allowed a far longer delivery (FIG. 3). It should be further noted that, as long as the nanoparticles maintained their integrity, they remained confined inside the gel (the size ratio between the nanoparticles and the fibrin mesh was around 10; NP=250 nm/gel mesh=25 nm).

The optimized degradation kinetics of the nanoparticles that compensated for the loss of enzyme due to its natural diffusion outside of the gel was further determined by modelisation. In order to optimize said kinetics, a regular delivery of the enzyme can be obtained using different pools of tailored nanoparticles. Indeed, as well known to the skilled person in the art, the size and the nature of the polymeric particles used to form a shell, notably in nanoparticles, can be tuned to deliver agents of interest (such as an enzyme, as proposed herein) from a few days to several weeks.

2.2. Introduction of a Glucose Polymer into the Hydrogel of the Invention 2.2.a) Glucose Polymer Influence on the Rheology of the Hydrogel The viscoelastic properties of the materials entrapping various starch sources were compared. Operating conditions were 1% imposed deformation at 1 Hz, cone/plate geometry (cone: diameter 25 mm, angle 2°), at 37° C. The addition of starch decreased the material elasticity depending on the starch origin. Potato starch displayed the highest destabilizing effect while corn and wheat starch had only a weak impact on the mechanical properties of the hydrogel (FIG. 4).

2.2.b) Introduction of High Amount of Glucose Polymer into the Hydrogel

Different concentrations of starch from various origins could be entrapped into the fibrin hydrogel. Depending on the nature of the starch, its chain length and structure differed and the starch concentration inside the gel was limited by the polysaccharide solubility.

The required glucose concentration could be obtained with rice wheat and corn starch with concentrations ≥3%, while potato starch had to be used at least at a 4% concentration (FIG. 5).

2.2.c) Glucose Release in High and Constant Concentration

With either 4% (w/V) wheat or corn starch entrapped in the fibrin hydrogel, a high enough glucose concentration for cell feeding was released from the gel for at least two weeks (FIG. 6A). Furthermore, a controlled release over 11 days can be obtained with 2% starch fibrin hydrogel (FIG. 6B).

2.3. Hydrogels of the Invention Improved Cell Survival In Vitro hMSC were genetically labelled with the luciferase (Luc) gene reporter and seeded (at $3.10^5$ cells per tissue constructs) within hydrogels containing fibrin (18 mg/ml, heat starch (4%), with or without enzyme ($2.10^{-4}$ µmol·min$^{-1}$·mg$^{-1}$) and with or without nanoparticles.

hMSC$^{Luc}$-containing hydrogels were then cultured in glucose-free culture medium (except for the glucose medium condition) and incubated in a near anoxic environment (pO2<0.1%) for 7 days. The bioluminescent (BLI) signal (expressed in photon/second) emitted by viable hMSC$^{Luc}$ was measured for each tested hydrogel using a bioluminescent imaging system. BLI signal from each hydrogel was normalized to those obtained from cell-containing fibrin (negative control).

In the presence of glucose-containing medium (positive control), the hMSC$^{Luc}$ viability was increased by 6 fold the presence of starch with or without empty (no enzyme) nanoparticles did not significantly increased cell viability compared to fibrin hydrogels. By contrast, when the enzyme was present, the hMSC$^{Luc}$ viability was after 7 days as good as the positive control (FIG. 7A).

However, when the viability was compared for a longer time, it has been shown that the viability of cells after 14 days is increased in hydrogels according to the invention by more than 100 time compared to fibrin hydrogels and by 2 times compared to glucose containing hydrogel (FIG. 7B).

Furthermore, it was also shown that hydrogels of the invention can increase the viability of adipose-derived stem cells (ADSC) and myoblasts (FIG. 7C).

2.4. Hydrogels of the Invention Improved Cell Survival In Vivo hMSC were genetically labelled with the luciferase (Luc) gene reporter. Hydrogel comprising hMSC$^{Luc}$ ($3.10^5$ cells per tissue constructs), fibrin (18 mg/ml, heat starch (4%), with or without enzyme ($2.10^{-4}$ µmol·min$^{-1}$·mg$^{-1}$) and with or without nanoparticles were subcutaneously implanted in the back of immunocompromised (Nude) mice. The bioluminescent (BLI) signal (expressed in photon/second) emitted by viable hMSC$^{Luc}$ was measured in each mouse at both day 1 and day 14 post-implantation using a bioluminescent imaging system.

In the absence of the enzyme, the BLI signal, and therefore the hMSC viability, dramatically decreased 7 days after implantation. By contrast, in the presence of the enzyme, the BLI signal emitted by viable hMSC$^{Luc}$ increased compared to day 1 indicating that the hMSC$^{Luc}$ not only survived but also proliferated within the hydrogels over the 7 day-period of implantation (FIG. 8A). 14 days (FIG. 8B) and 28 days (FIG. 8C) after implantation the BLI signal emitted by viable hMSC$^{Luc}$ is more than 30 time higher compared to fibrin hydrogel.

Those results were also observed with a lower concentration of glucose polymer (e.g. 1%). Furthermore, incorporation of the enzyme within the NPs greatly improved the hMSC$^{Luc}$ proliferation.

Moreover, it was shown that the hydrogels of the invention improve the survival of biological material (hMSCs) loaded within the hydrogel in in vivo ischemic conditions. An haematoxylin counterstain allows to observe the hydrogels infiltration by host cells (stain by haematoxylin but not by beta2-microglobulin) (FIG. 9A). Beta2-microglobulin immunostaining (specific of hMSCs) showed a significant increase (7.5 fold) of viable hMSCs after 14 days in hydrogels containing Fibrin/starch/AMG in comparison to hydrogels containing Fibrin, as confirmed by the quantification of viable hMSCs in hydrogels (FIG. 9B).

2.5. Introduction of Coral Inside the Hydrogel of the Invention

A good homogeneity of the coral repartition inside the hydrogel was achieved with hydrogels comprising wheat starch (FIG. 10).

2.6. Stability of the Kit Components

The kit components showed a good stability over 28 days as confirmed by the good mechanical properties of the resulting hydrogel (FIG. 11). The activity of the enzyme AMG was preserved after 14 days storage allowing a long term storage of the kit components.

3. Conclusion

The Inventors successfully developed a mixed hydrogel of fibrin and starch displaying homogeneous structure, a lack of syneresis and good mechanical properties, in the presence of relatively elevated concentration of starch. Starch retention of up to 60 mg/mL could be reached.

More particularly, said gel may is capable to contain nanoparticles encapsulating an enzyme hydrolysing starch into glucose, which allowed the diffusion of glucose in a near linear manner for at least 16 days. The presence of the nanoparticles did not alter the activity of the enzyme.

The hydrogel of the invention may also comprise biological material, such as cells. In vitro and in vivo data showed that such gel could be used to promote cell survival in ischemic conditions, and may therefore be used in therapies requiring cell or tissue regeneration.

This time-controlled release system, which allows a gradual hydrolysis of starch into glucose, displays far greater properties on cellular activity in hypoxic conditions than a direct exogenous glucose delivery.

REFERENCES

Ahmed E M (2013). Hydrogel: Preparation, characterization, and applications. *Journal of Advanced Research.*
Anitua E, Sanchez M, Nurden A T, Nurden P, Orive G, and Andia I (2006). *Trends Biotechnol.;* 24:227-234.
Baldmin S P, and Saltzman W M (1998). *Adv Drug Deliver Rev.;* 33:71-86.
Bensaïd W, Triffitt J T, Blanchat C, Oudina K, Sedel L, Petite H. (2002). *Biomaterials;* 24:2497-2502.
Cheng C J, and Saltzman W M (2012). *Mol. Pharmaceutics;* (9): 1481-1488.
Dainiak M. B., Allan I U, Savina I N, Cornello L, James E S, James S L, JAMES, Mikhalovsky S V, Jungvid H, and Galaev I Y. (2010). *Biomaterial;* 31(1): 67-76.
Das N (2013). *International Journal of Pharmaceutical Sciences;* 5(3): 112-117.
De Gennes P G (1979). *Scaling concepts in polymer physics*, Cornell University Press, pp 0-324.
Deschepper M, Oudina K, David B, Myrtil V, Collet C, Bensidhoum M, Logeart-Avramoglou D, and Petite H (2011). *J Cell Mol Med.;* 15(7):1505-14.
Deschepper M, Manassero M, Oudina K, Paquet J, Monfoulet L E, Bensidhoum M, Logeart-Avramoglou D, and Petite H (2013). *Stem Cells;* 31(3):526-35.
Fernandez C E, Achneck H E, Reichert W M, and Truskey G A (2014). *Curr Opin Chem Eng.;* 3:83-90.
Friedenstein A J, Chailakhyan R K, and Gerasimov U V. (1987). *Cell Tissue Kinet,* 20(3), 63 272.
Garg T, Singh O, Arora S, and Murthy R (2012). *Crit Rev Ther Drug Carrier Syst.;* 29(1):1-63.
Hartgerink J D, Beniash E, and Stupp S I (2001). *Science;* 294: 1684-1688.
Jane J L, and Chen J F (1992). *Cereals Chem.,* 69:60.
Klak M C, Lefebvre E, Rémy L, Agniel R, Picard J, Giraudier S, and Larreta Garde V (2013). *Macromolecular Bioscience;* 6: 687-95.
Klak M C, Picard J, Giraudier S, and Larreta Garde V (2012). *Soft Matter;* 8: 4750-4755.
Konofaos P., and Ver Halen J P (2013). *J Reconstr Microsurg.;* 29(3):149-64.
Lauffer M A (1961). *Biophys. J.;* 1: 205-13.
Li S, Sengupta D, and Chien S. (2013). *Rev Syst Biol Med.;* 6(1):61-76.
Linnes M P, Ratner B D, and Giachelli C M (2007). *Biomaterials;* 28:5298-5306.
Lundberg M S (2013). *Circ Res.;* 112(8):1097-103.
Neal R A, Jean A, Park H, Wu P B, Hsiao J, Engelmayr G C, Langer R, and Freed L E (2013). *Tissue engineering;* Part A (19): 5-6, 793-807.
Oliveira M B, and Mano J F (2011). *Biotechnology Progress;* (27): 4, 897-912.
Papon P J, Leblond and P. Meijer (2006). Gelation and Transitions in Biopolymers. The Physics of Phase Transitions. Dunod. Berlin Heildelberg, Springer-Verlag: 189-213.
Ronfard V, Rives J M, Neveux Y, Carsin H, and Barrandon Y (2000). *Transplantation;* 70:1588-1598.
Rosso F, Marino G, Giordano A, Barbarisi M, Parmeggiani D, and Barbarisi A (2005). *J. Cell. Physiol.;* 203:465-470.
Seguchi M, Higasa T, and Mori T. (1994). *Cereals Chem.,* 71:636.
Sinha V R, and Trehan A (2003). *J Control Release;* 90:261-280.
Singh N, Inouchi N, and Nishinari K. (2005). *J Agric Food Chem.;* 53(26):10193-9.
Soppimath K S, Aminabhavi T M, Kulkarni A R, and Rudzinski W E (2001). *J Control Release;* 70:1-20.
Sperling L H and Misha V (1997). IPNs around the world: science and engineering, Wiley, p. 1-25.
Steinbach J M, Weller C E, Carmen J B, and Saltzman W M (2012). *Journal of Controlled Release;* 162:102-110.
Tang C, Qiu F, and Zhao X (2013). *Journal of Nanomaterials;* Volume 2013, Article ID 469261, Xia W, Liu W, Cui L, Liu Y, Zhong W, Liu D, Wu J, Chua K and Cao Y (2004). *Journal of Biomedical Materials Research. Part B: Applied Biomaterials;* 71B (2): 373-380.

Yang S, Leong K F, Du Z, and Chua C K (2002). *Tissue Engineering;* 8(1): 1-11.

Zhao X and Zhang S (2007). *Macromolecular Bioscience;* 7(1):13-22.

Zimmermann W H, and Eschenhagen T. (2003). *Heart Fail Rev.;* 8(3):259-69.

The invention claimed is:

1. A time-controlled glucose releasing hydrogel, comprising:
   a) a water-containing gelified polymer;
   b) a glucose polymer entrapped in polymer a); and
   c) at least one enzyme capable of hydrolyzing the glucose polymer b) into glucose, said enzyme being entrapped in polymer a).

2. The hydrogel according to claim 1, wherein said polymer a) is a protein polymer selected from the group consisting of water-containing gelified silk proteins, soy proteins, milk proteins, wheat proteins, linen proteins, egg proteins, albumin, elastin, myosin, actin, myoglobin, polylysine, polyglutamine, self-assembling peptides, proteins comprising RGD sequence(s), and derivatives thereof.

3. The hydrogel according to claim 2, wherein said protein comprising RGD sequence(s) is fibrin.

4. The hydrogel according to claim 3, wherein the concentration of fibrin is ranging from about 2.5 mg/ml to about 90 mg/ml.

5. The hydrogel according to claim 1, wherein said polymer a) is a synthetic polymer selected from the group consisting of water-containing gelified polyethylene oxide (PEO), polyacrylic acid (PAA), polypropylene oxide (PPO), polyethyl hydroxide (PEH), polyvinyl alcohol (PVA), N-isopropylacrylamide (NIPAM), polyacrylamide (PAM), polyvinyl sulfone (PVS), and derivatives thereof.

6. The hydrogel according to claim 1, wherein said glucose polymer b) is selected from the group consisting of starch, amylose, amylopectin, glycogen, maltodextrins, cyclodextrins polymers, isomaltose polymers, icodextrins, malto-oligosaccharides, dextran, cellulose, and derivatives thereof.

7. The hydrogel according to claim 6, wherein said glucose polymer is starch.

8. The hydrogel according to claim 7, wherein the concentration of starch is ranging from about 1% (w/v) to about 10% (w/v).

9. The hydrogel according to claim 1, wherein said enzyme is selected from the group consisting of α-glucosidases, β-glucosidases, dextrinases, maltodextrinases, α-amylases, β-amylases, maltohydrolases, cellobiosidases, and combinations thereof.

10. The hydrogel according to claim 1, wherein said enzyme is entrapped within polymeric particles in polymer a).

11. The hydrogel according to claim 10, wherein said polymeric particles are nanoparticles.

12. The hydrogel according to claim 10, wherein said polymeric particles are selected from the group consisting of alginate, chitin, gelatin, collagen, albumin, poly(lactic) acid (PLA), poly(glycolic) acid (PGA), poly(lactic-co-glycolic) acid (PLGA), polyhydroxybutyrate (PHB), poly(hy-d roxybutyrate-co-valerate) (PHBV), polycaprolactone (PCL), poly(methyl methacrylate) (PMMA), poly(cyanoacrylate) (PCA) polymeric particles, and derivatives thereof.

13. The hydrogel according to claim 1, further comprising at least one biological material, said material being entrapped in said hydrogel.

14. The hydrogel according to claim 13, wherein said biological material is selected from the group consisting of cells, tissues, stromata, derivatives thereof, and combinations thereof.

15. A medical device, comprising the hydrogel as defined in claim 1.

16. The device according to claim 15, wherein said device is selected from the group consisting of a patch, a bandage, and an implant.

17. A method for treating a disorder in a subject in need thereof, comprising:
   (i) administering to said subject a time-controlled glucose releasing hydrogel, comprising:
      a) a water-containing gelified polymer;
      b) a glucose polymer entrapped in polymer a); and
      c) at least one enzyme capable of hydrolyzing the glucose polymer b) into glucose, said enzyme being entrapped in polymer a); or
   (ii) using on said subject a medical device comprising a time-controlled glucose releasing hydrogel, comprising:
      d) a water-containing gelified polymer;
      e) a glucose polymer entrapped in polymer d); and
      f) at least one enzyme capable of hydrolyzing the glucose polymer e) into glucose, said enzyme being entrapped in polymer d).

18. A method of tissue regeneration in a subject in need thereof, comprising:
   (i) administering to said subject a time-controlled glucose releasing hydrogel, comprising:
      a) a water-containing gelified polymer;
      b) a glucose polymer entrapped in polymer a); and
      c) at least one enzyme capable of hydrolyzing the glucose polymer b) into glucose, said enzyme being entrapped in polymer a); or
   (ii) using on said subject a medical device comprising a time-controlled glucose releasing hydrogel, comprising:
      d) a water-containing gelified polymer;
      e) a glucose polymer entrapped in polymer d); and
      f) at least one enzyme capable of hydrolyzing the glucose polymer e) into glucose, said enzyme being entrapped in polymer d).

19. A method for preparing the hydrogel as defined in claim 1, comprising the step of mixing:
   a) a water-soluble gellable monomer or polymer;
   b) a glucose polymer; and
   c) at least one enzyme capable of hydrolyzing the glucose polymer b) into glucose.

20. A kit, comprising:
   d) a water-soluble gellable monomer or polymer;
   e) a glucose polymer; and
   f) at least one enzyme capable of hydrolyzing the glucose polymer b) into glucose.

* * * * *